(12) United States Patent
He et al.

(10) Patent No.: US 11,969,821 B2
(45) Date of Patent: Apr. 30, 2024

(54) SURFACE TEXTURING USING ENERGY PULSES

(71) Applicant: Medtronic, Inc., Minneapolis, MN (US)

(72) Inventors: Xiangnan He, Chandler, AZ (US); David A. Ruben, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/067,438

(22) Filed: Dec. 16, 2022

(65) Prior Publication Data
US 2023/0120034 A1  Apr. 20, 2023

Related U.S. Application Data

(62) Division of application No. 16/353,119, filed on Mar. 14, 2019, now Pat. No. 11,548,092.
(Continued)

(51) Int. Cl.
*B23K 26/122* (2014.01)
*B23K 26/046* (2014.01)
(Continued)

(52) U.S. Cl.
CPC ........ *B23K 26/0622* (2015.10); *B23K 26/046* (2013.01); *B23K 26/0624* (2015.10);
(Continued)

(58) Field of Classification Search
CPC .. B23K 26/082; B23K 26/122; B23K 26/127; B23K 26/355; B23K 26/046; B23K 26/0622; B23K 26/0624; A61N 1/04
See application file for complete search history.

(56) References Cited

U.S. PATENT DOCUMENTS

| 5,473,138 A | 12/1995 | Singh et al. |
|---|---|---|
| 5,558,789 A | 9/1996 | Singh |

(Continued)

FOREIGN PATENT DOCUMENTS

| CN | 102006964 A | 4/2011 |
|---|---|---|
| CN | 104339088 A | 2/2015 |

(Continued)

OTHER PUBLICATIONS (PCT/US2019/022200) PCT Notification of Transmittal of the International Search Report and the Written Opinion of the International Searching Authority, dated Jul. 25, 2019, 13 pages.
(Continued)

*Primary Examiner* — Dana Ross
*Assistant Examiner* — Kuangyue Chen
(74) *Attorney, Agent, or Firm* — Shumaker & Sieffert, P.A.

(57) ABSTRACT

A system includes an energy source, a focusing system, and a controller. The energy source is configured to output energy pulses to the focusing system. A chamber surrounds at least a portion of a metallic substrate and contain a liquid in contact with a surface of the metallic substrate. The controller is configured to cause the energy source to output energy pulses and cause the focusing system to focus a focal volume of the energy pulses at or near the surface of the metallic substrate that is in contact with the liquid to create micro-scale or smaller surface texturing on the metallic substrate.

14 Claims, 24 Drawing Sheets

Related U.S. Application Data

(60) Provisional application No. 62/644,734, filed on Mar. 19, 2018.

(51) Int. Cl.

| | |
|---|---|
| *B23K 26/0622* | (2014.01) |
| *B23K 26/082* | (2014.01) |
| *B23K 26/12* | (2014.01) |
| *B23K 26/352* | (2014.01) |
| *A61N 1/04* | (2006.01) |

(52) U.S. Cl.
CPC .......... *B23K 26/082* (2015.10); *B23K 26/122* (2013.01); *B23K 26/127* (2013.01); *B23K 26/355* (2018.08); *A61N 1/04* (2013.01)

(56) References Cited

U.S. PATENT DOCUMENTS

| | | | |
|---|---|---|---|
| 7,442,629 B2 | 10/2008 | Mazur et al. | |
| 7,884,446 B2 | 2/2011 | Mazur et al. | |
| 8,158,493 B2 | 4/2012 | Shah et al. | |
| 8,598,051 B2 | 12/2013 | Mazur et al. | |
| 8,685,185 B2 | 4/2014 | Guo et al. | |
| 8,846,551 B2 | 9/2014 | Gupta et al. | |
| 9,102,007 B2 | 8/2015 | Hosseini | |
| 9,136,146 B2 | 9/2015 | Mazur et al. | |
| 9,289,594 B2 * | 3/2016 | Petersen | B23K 26/355 |
| 10,350,705 B2 | 7/2019 | Landon et al. | |
| 2008/0216926 A1 | 9/2008 | Guo et al. | |
| 2008/0299408 A1 | 12/2008 | Guo et al. | |
| 2010/0143744 A1 | 6/2010 | Gupta et al. | |
| 2013/0081951 A1 | 4/2013 | Hankey et al. | |
| 2014/0314995 A1 * | 10/2014 | Liu | B23K 26/009 |
| | | | 219/121.72 |
| 2015/0173635 A1 | 6/2015 | Fisk | |
| 2015/0202712 A1 | 7/2015 | Seghi et al. | |
| 2019/0283176 A1 | 9/2019 | He et al. | |

FOREIGN PATENT DOCUMENTS

| | | | |
|---|---|---|---|
| CN | 106573336 A | 4/2017 | |
| DE | 4324185 A1 | 1/1995 | |
| DE | 102007010872 A1 | 9/2008 | |
| DE | 102013002977 B3 | 12/2013 | |
| JP | H0827584 A | 1/1996 | |
| WO | 2008041692 A1 | 4/2008 | |
| WO | WO-2008041692 A1 * | 4/2008 | ......... B23K 26/0006 |

OTHER PUBLICATIONS

First Office Action and Search Report, and translation thereof, from counterpart Chinese Application No. 201980020280.3 dated Mar. 7, 2022, 15 pp.

Prosecution History from U.S. Appl. No. 16/353,119, dated Mar. 11, 2021 through Sep. 28, 2022, 66 pp.

Communication pursuant to Article 94(3) EPC from counterpart European Application No. 19713981.9 dated Mar. 21, 2023, 7 pp.

Response to Communication pursuant to Article 94(3) EPC dated Mar. 21, 2023, from counterpart European Application No. 19713981.9 filed Jul. 18, 2023, 14 pp.

* cited by examiner

FIG. 7A
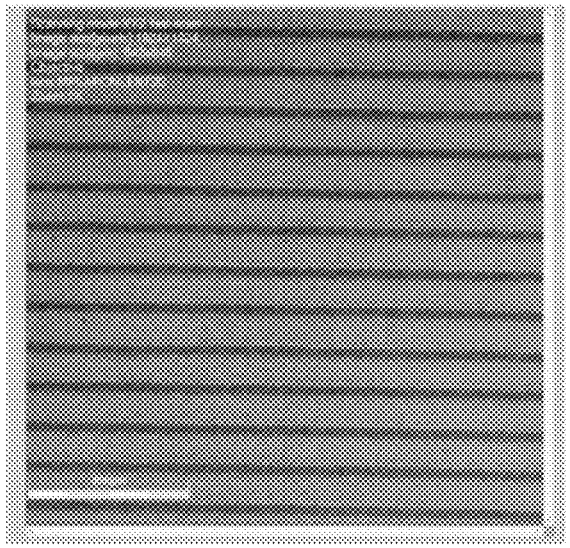
FIG. 7B
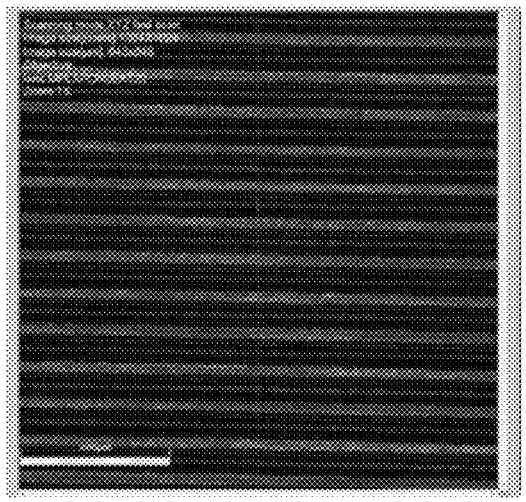
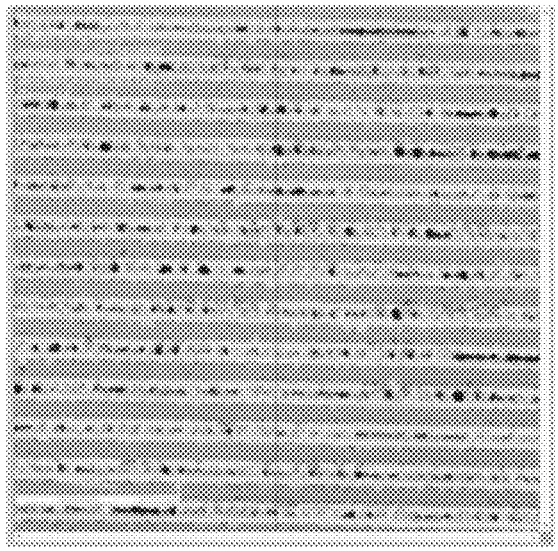
FIG. 7C
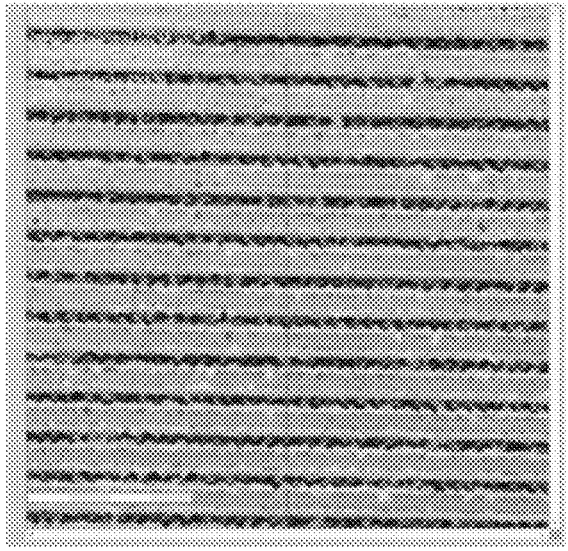
FIG. 7D

FIG. 8A
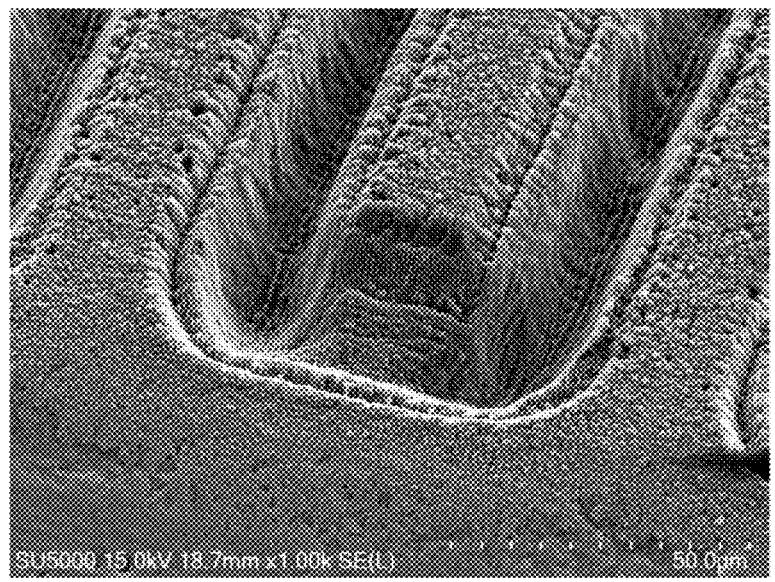
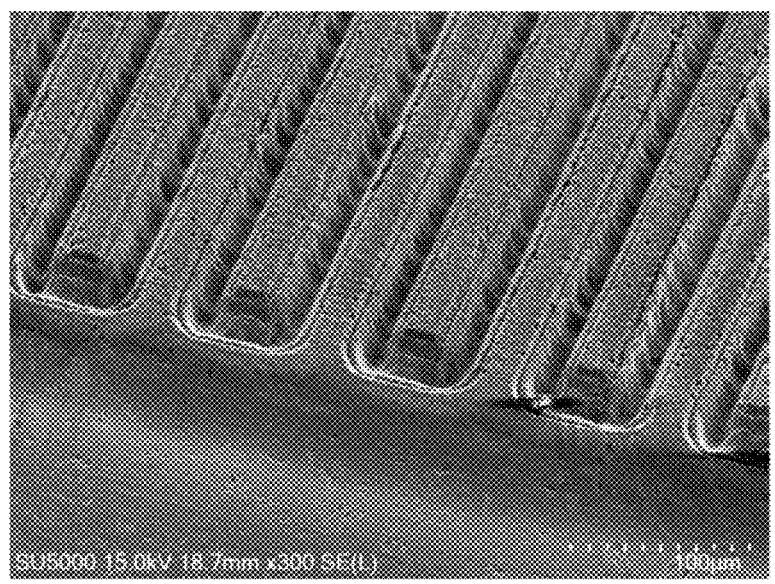
FIG. 8B

FIG. 12A
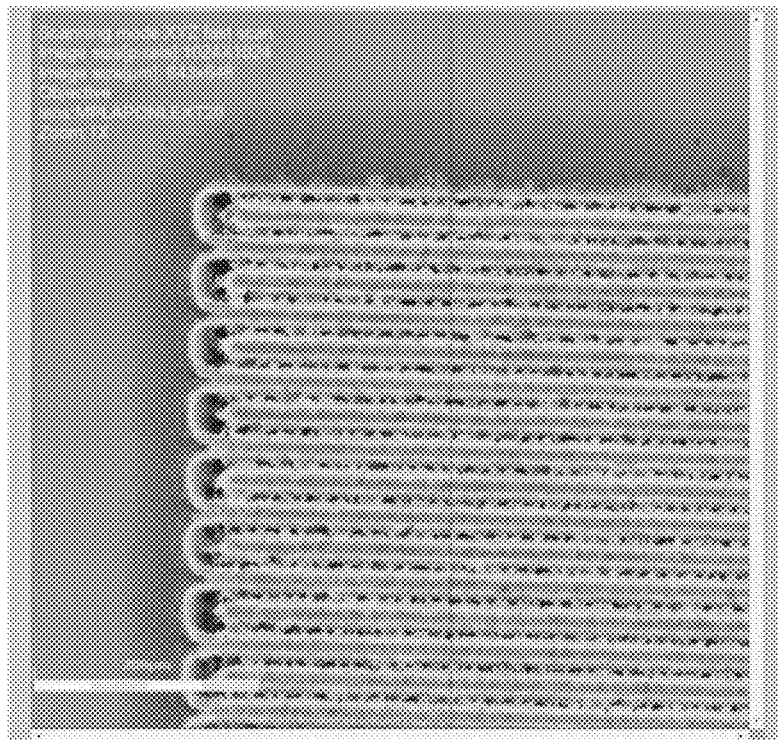
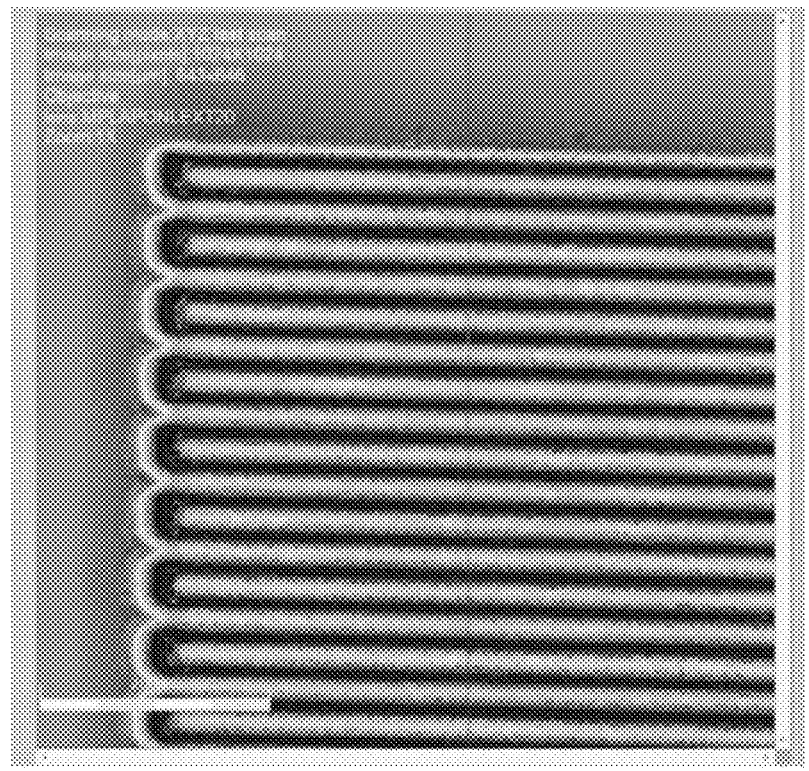
FIG. 12B

FIG. 13A
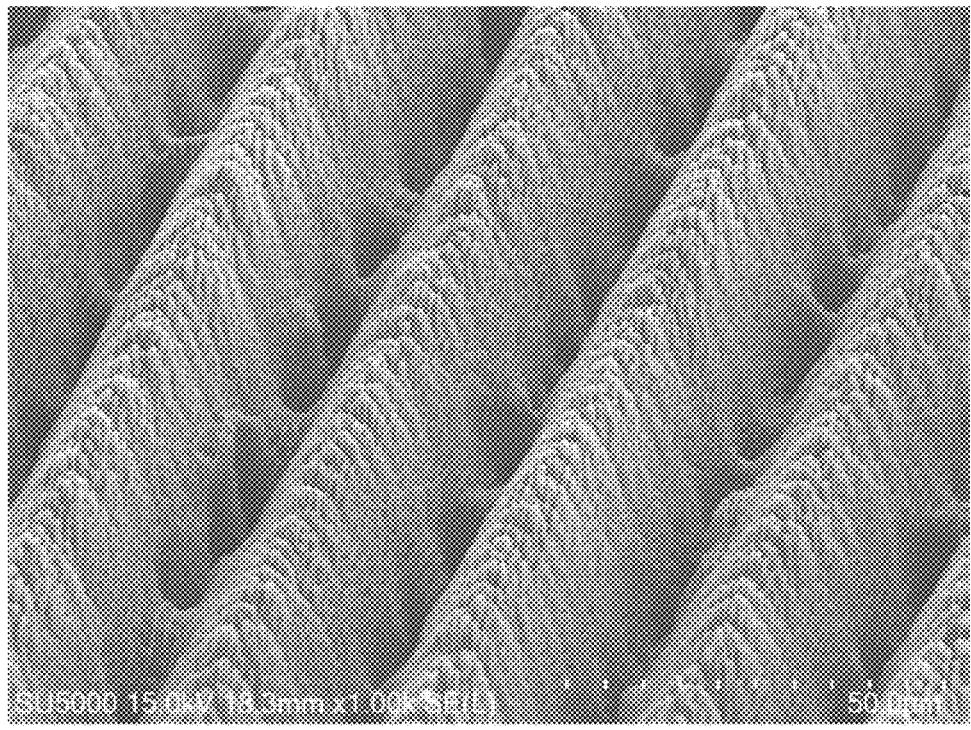
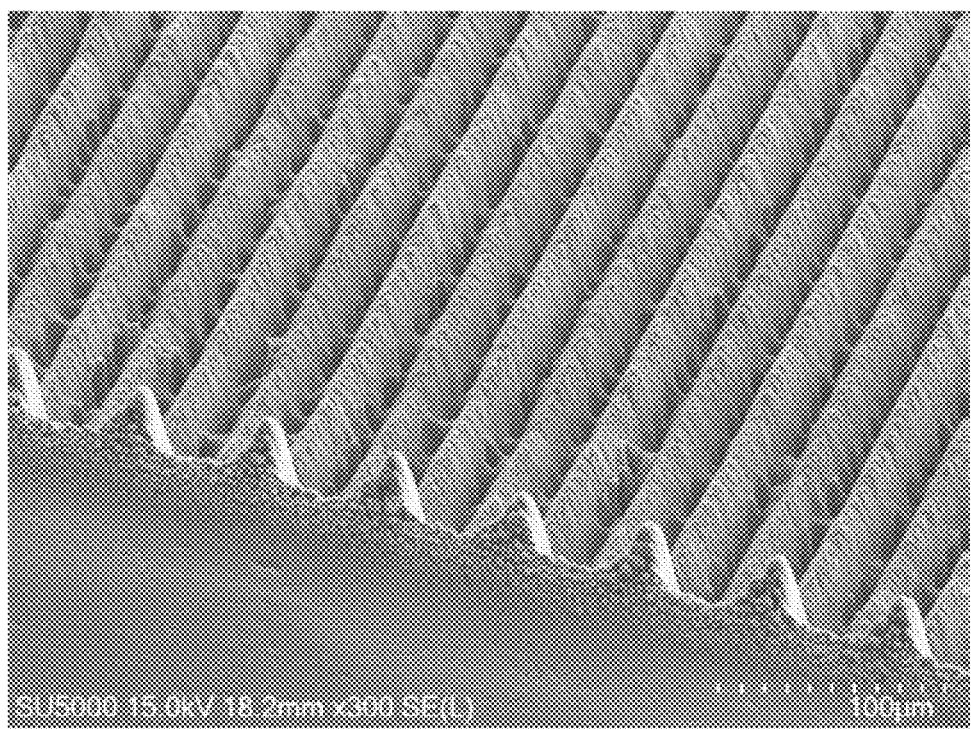
FIG. 13B

FIG. 14A
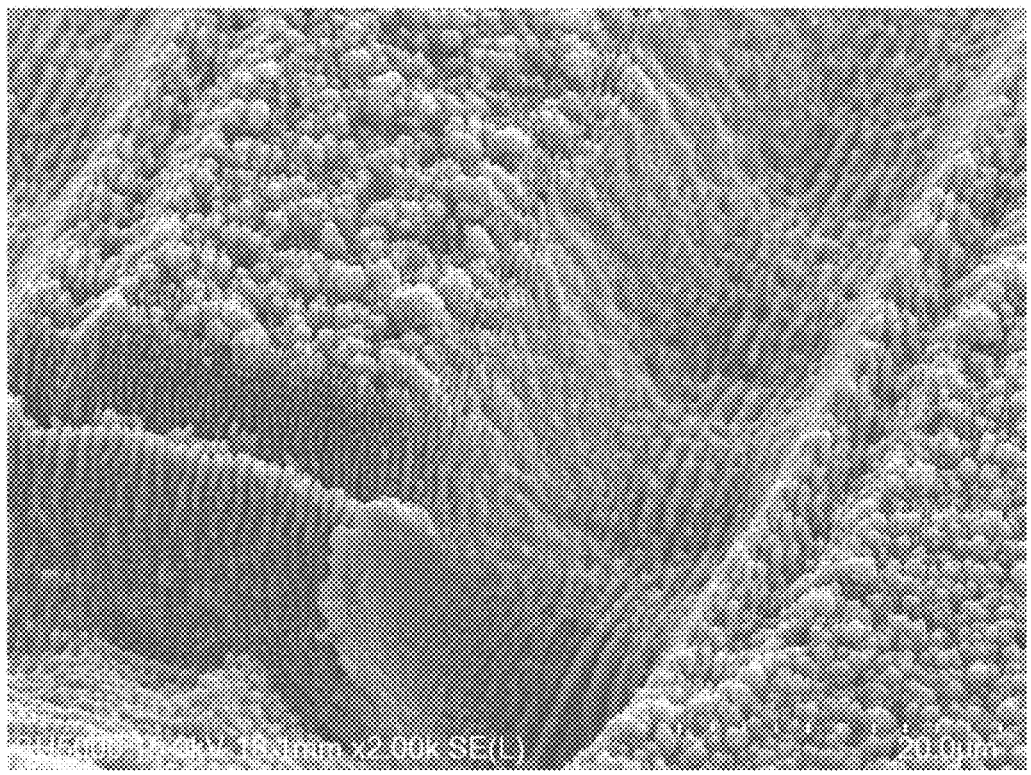
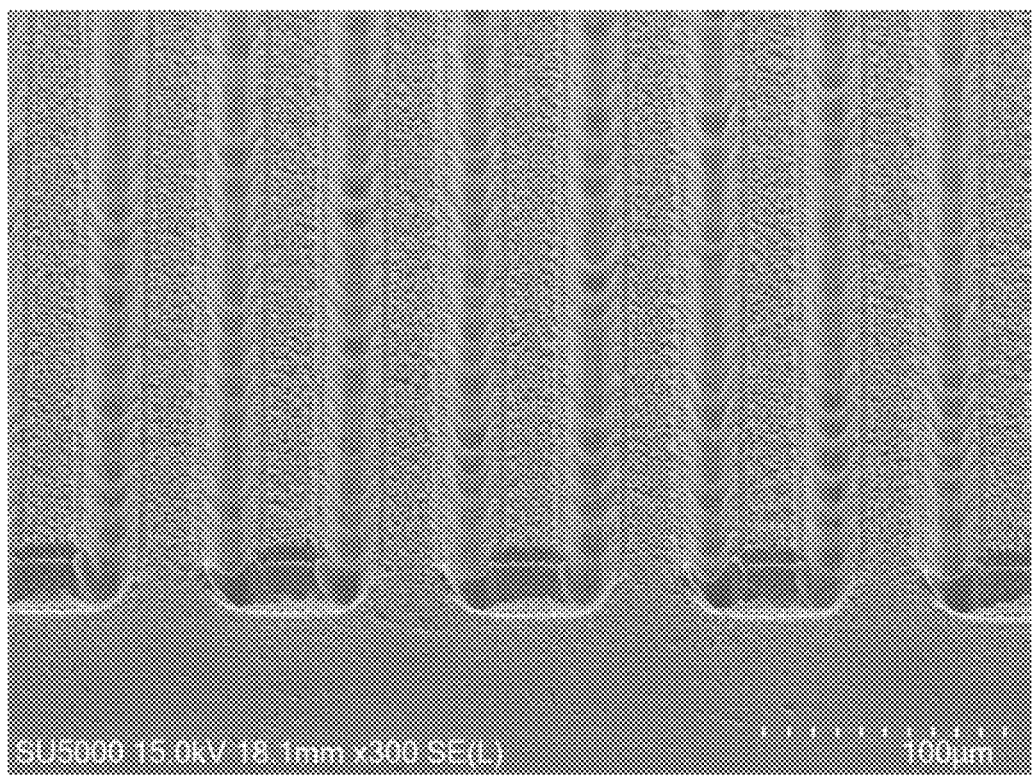
FIG. 14B

FIG. 16A
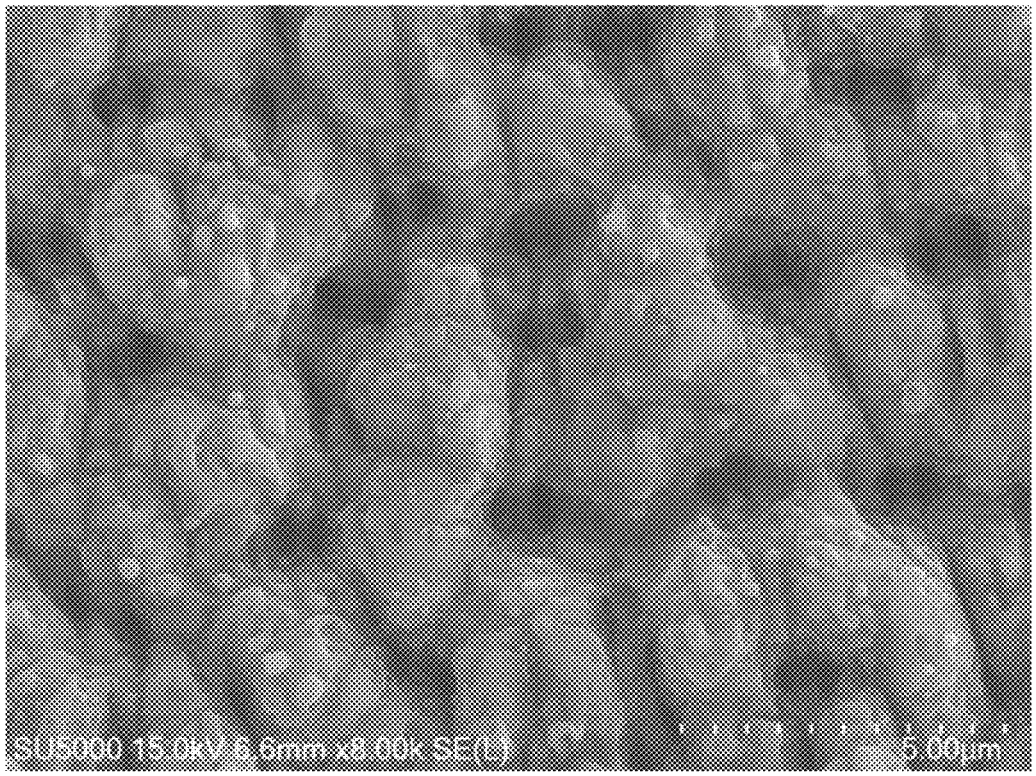
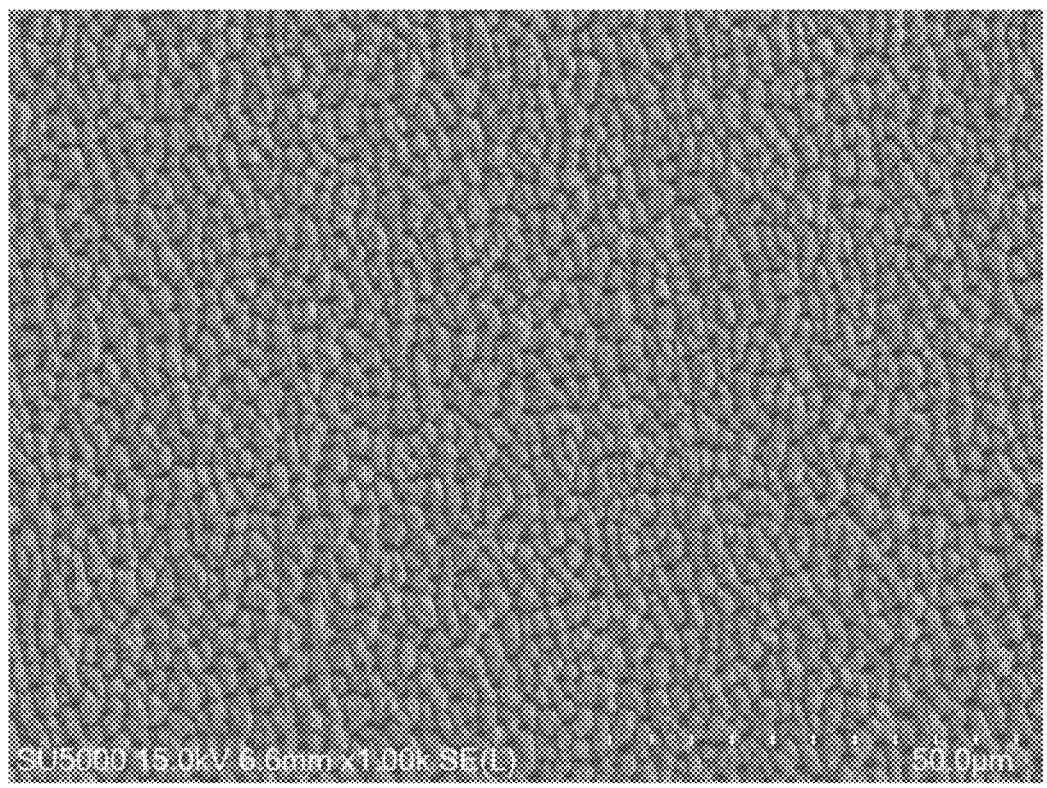
FIG. 16B

FIG. 17A
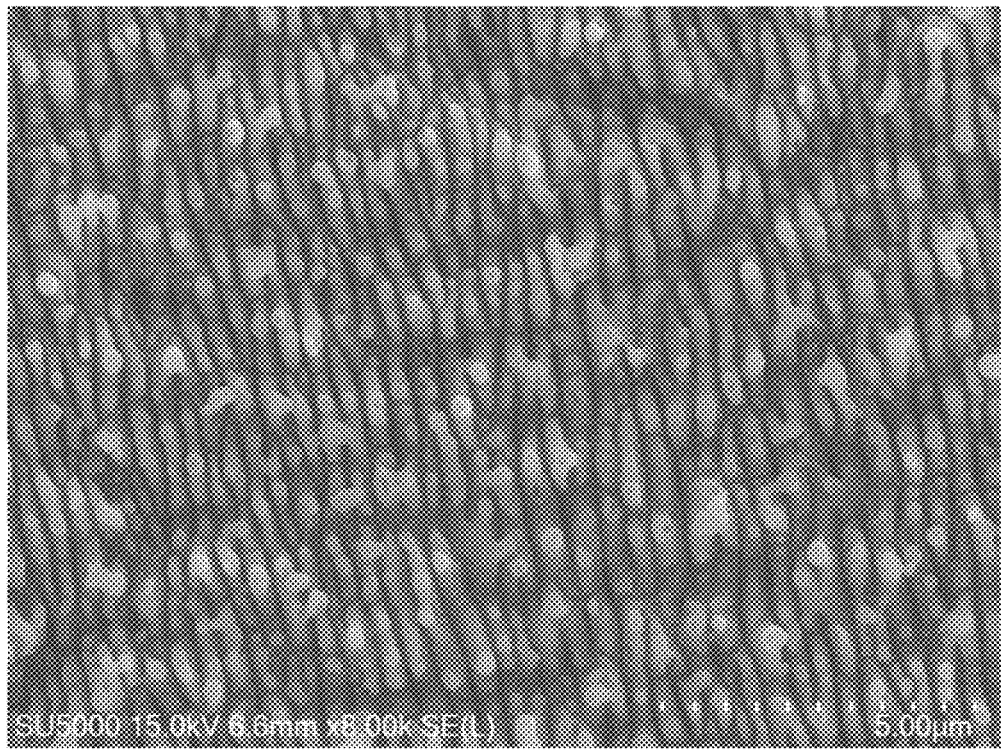
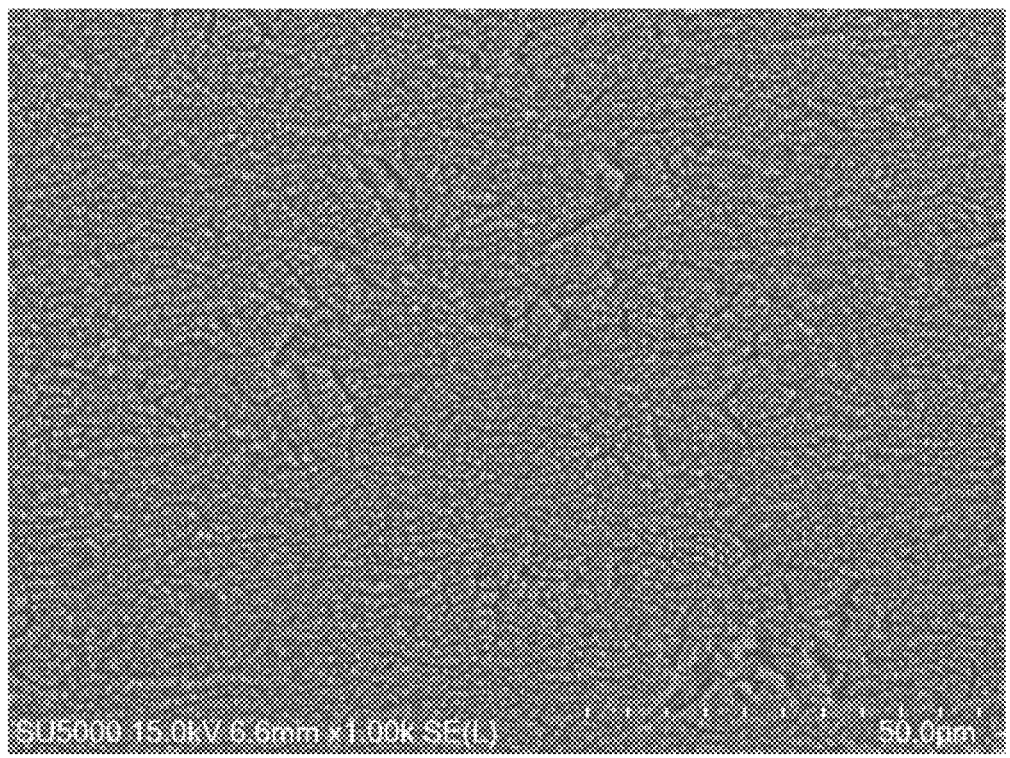
FIG. 17B

FIG. 18A
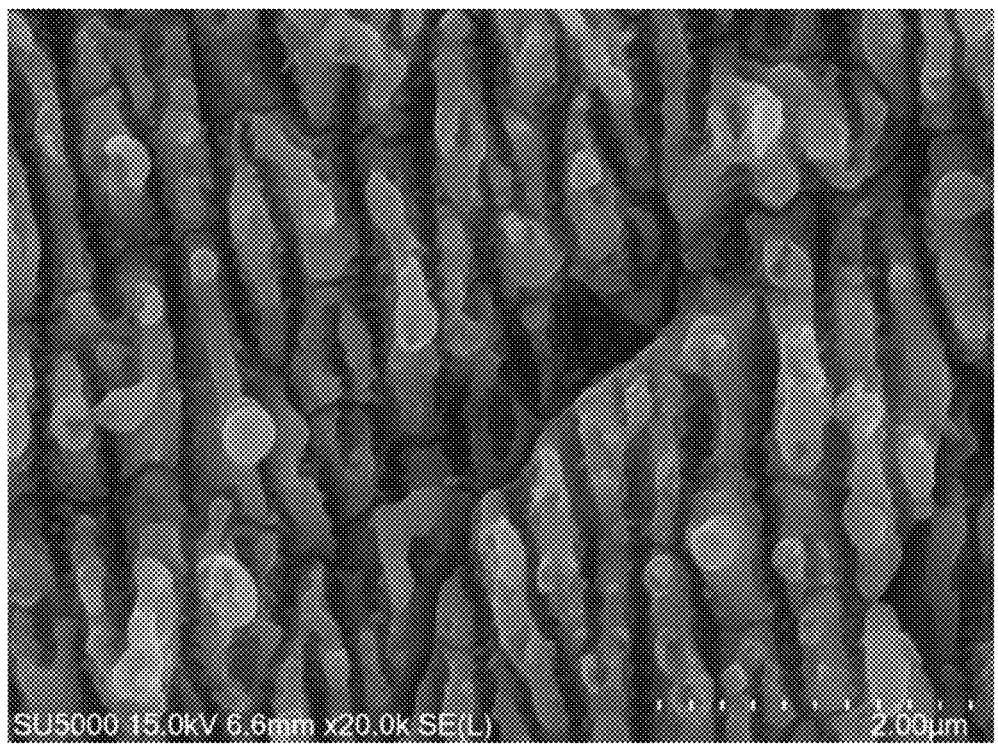
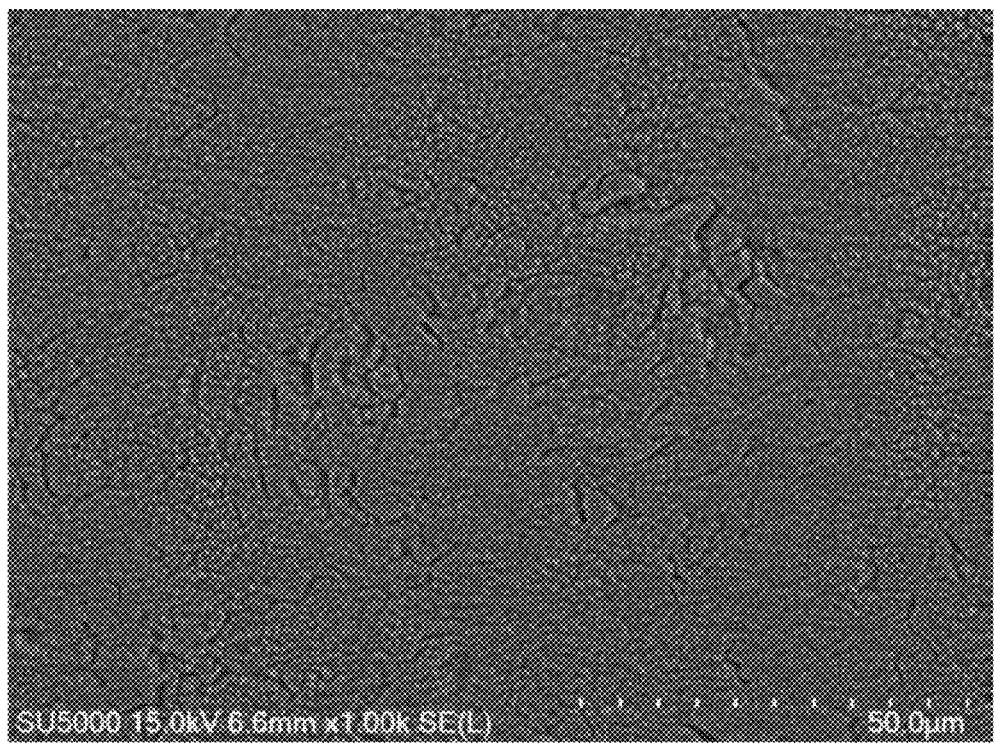
FIG. 18B

FIG. 19A
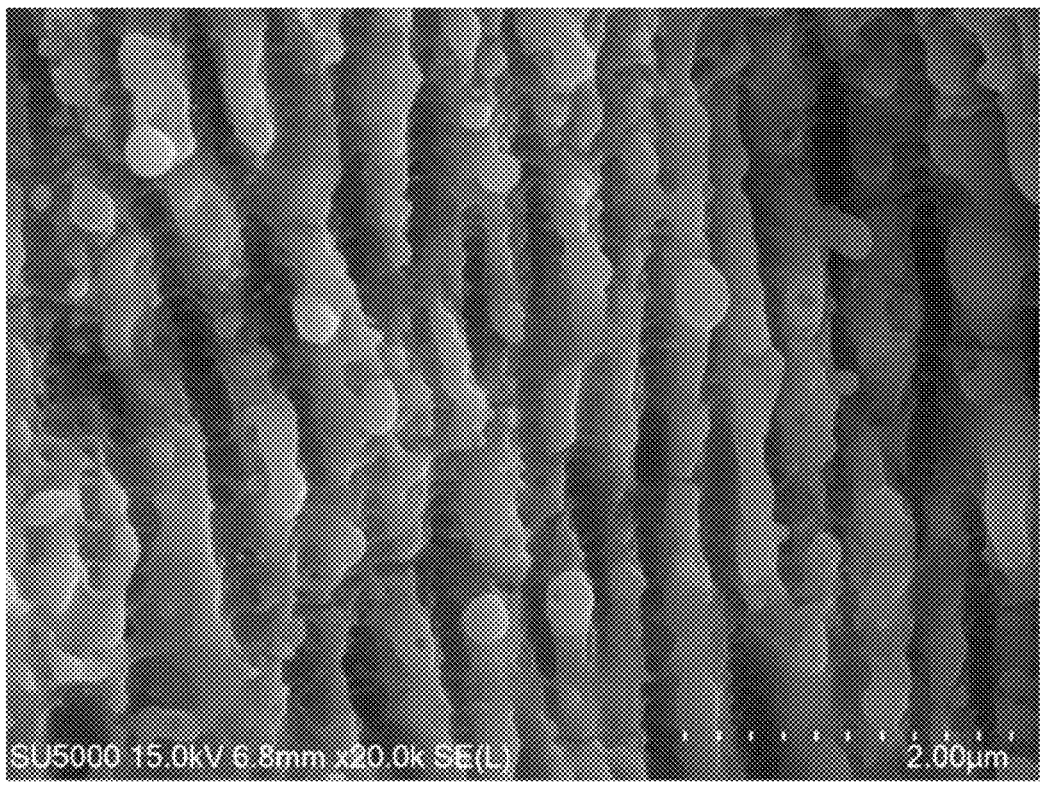
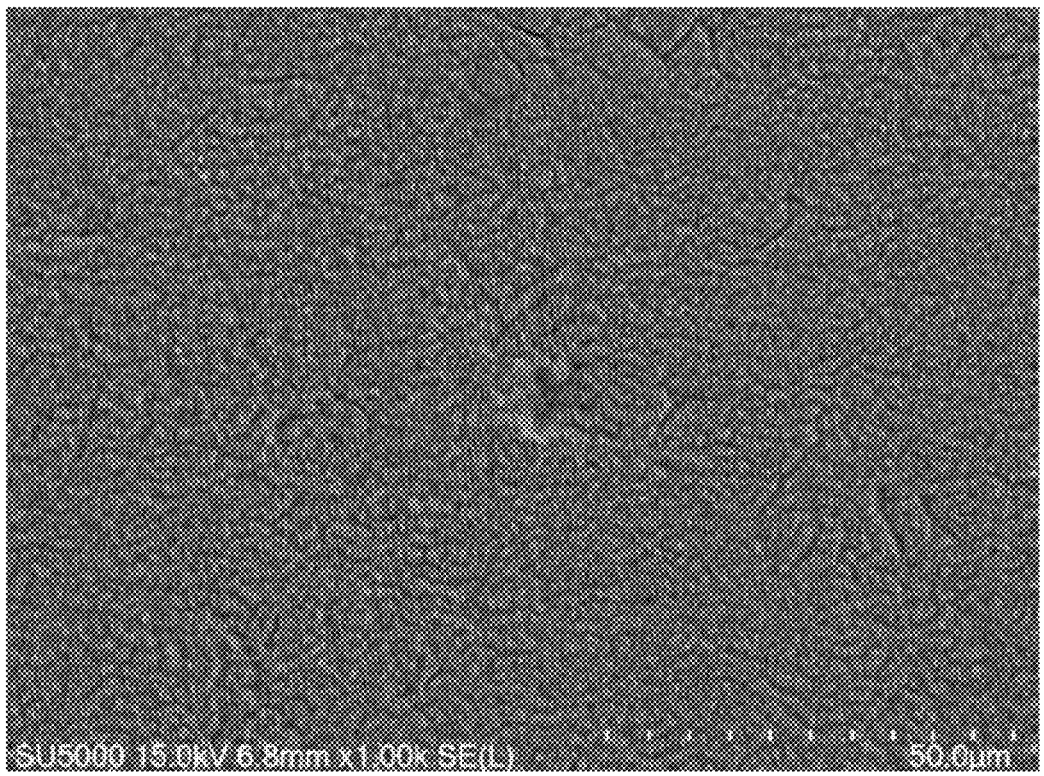
FIG. 19B

SURFACE TEXTURING USING ENERGY PULSES

CROSS-REFERENCE TO RELATED APPLICATIONS

This application is a Divisional of U.S. application Ser. No. 16/353,119, filed Mar. 14, 2019, which claims the benefit of U.S. Provisional Application No. 62/644,734, filed Mar. 19, 2018, the entire contents of each of which are incorporated by reference herein.

TECHNICAL FIELD

The disclosure relates to techniques for texturing a surface of a metallic substrate.

BACKGROUND

Surfaces of materials may be textured to increase surface area, modify adhesion or hydrophobicity, or the like. For example, surfaces may be selectively etched to form three-dimensional structures in the substrate.

SUMMARY

In some examples, the disclosure describes a system including a focusing system, an energy source, a chamber, and a controller. The energy source may be configured to output energy pulses to the focusing system. The chamber may surround at least a portion of a metallic substrate and contain a liquid in contact with a surface of the metallic substrate. The controller may be configured to cause the energy source to output energy pulses to the focusing system and cause the focusing system to focus a focal volume of the energy pulses at or near the surface of the metallic substrate that is in contact with the liquid to create micro-scale or smaller surface texturing on the metallic substrate.

In some examples, the disclosure describes a method that includes causing, by a controller, an energy source to output energy pulses to a focusing system. The method also may include causing, by the controller, the focusing system to focus a focal volume of the energy pulses at or near a surface of a metallic substrate in contact with a liquid to create micro-scale or smaller surface texturing on the surface of the metallic substrate that is in contact with the liquid, where the liquid and the metallic substrate are contained in a chamber.

In some examples, the disclosure describes a non-transitory computer-readable medium including instructions that, when executed, cause one or more processors of a controller to control an energy source to output energy pulses to a focusing system and control the focusing system to focus a focal volume of the energy pulses at or near a surface of a metallic substrate in contact with a liquid to create micro-scale or smaller surface texturing on the surface of the metallic substrate that is in contact with the liquid, where the liquid and the metallic substrate are contained in a chamber.

The details of one or more examples are set forth in the accompanying drawings and the description below. Other features, objects, and advantages of the disclosure will be apparent from the description and drawings, and from the claims.

BRIEF DESCRIPTION OF DRAWINGS

FIGS. 7A-7E are images illustrating samples of Ti foils energy textured in air.

FIGS. 8A and 8B are images illustrating samples of Ti foil energy textured in air.

FIGS. 12A and 12B are micrographs of surface morphology on substrates completed with energy pulses in a nitrogen environment and a different number of cycles.

FIGS. 13A and 13B are micrographs at different resolutions illustrating surface morphology on the Ti foil shown in FIG. 12A.

FIGS. 14A and 14B are micrographs at different resolutions illustrating surface morphology on a Ti foil completed with energy pulses in a nitrogen environment.

FIGS. 16A and 16B are micrographs at different magnifications illustrating surface morphology of a Ti foil energy textured in water.

FIGS. 17A and 17B are micrographs at different magnifications illustrating surface morphology of a Ti foil energy textured in water.

FIGS. 18A and 18B are micrographs at different magnifications illustrating surface morphology of a Ti foil energy textured in diluted hydrogen peroxide.

FIGS. 19A and 19B are micrographs at different magnifications illustrating surface morphology of a Ti foil energy textured in diluted hydrogen peroxide.

DETAILED DESCRIPTION

In general, the disclosure describes example techniques related to increasing the surface area of a substrate by using energy pulses to texture the surface. In some examples, the substrate may be a metallic substrate such as an electrode. In some examples, electrodes may have a functional surface that is for sensing or stimulating. Sensing and stimulating may be facilitated by increasing the electrode surface area, thus increasing the capacitance of the electrode. The techniques described herein utilize a liquid environment in contact with the surface to be textured to affect the texturing process. By using a liquid environment, smaller surface features may be formed than in a gaseous environment with similar energy pulse properties. For example, using energy pulses having a femto- or picosecond pulse duration in a liquid medium may result in surface texturing with microscale or smaller surface features.

The system may include an energy source, which outputs the energy pulses, a focusing system, which may focus the energy pulses at or near selected locations on the surface, and a controller, which controls operation of the energy source and the focusing system. The focusing system may focus the energy pulses at the interface of the surface and the liquid or may focus the energy pulses near the interface of the surface and the liquid (e.g., within about 500 microns away from the surface) such that the energy pulses are defocused at the interface of the surface and the liquid.

In some examples, the energy pulses may modify both surface chemistry and surface morphology of the substrate. For example, during the surface texturing, oxygen or nitrogen from the liquid may react with the metallic substrate to form a metal oxide or nitride on the surface of the substrate.

Figure 1:
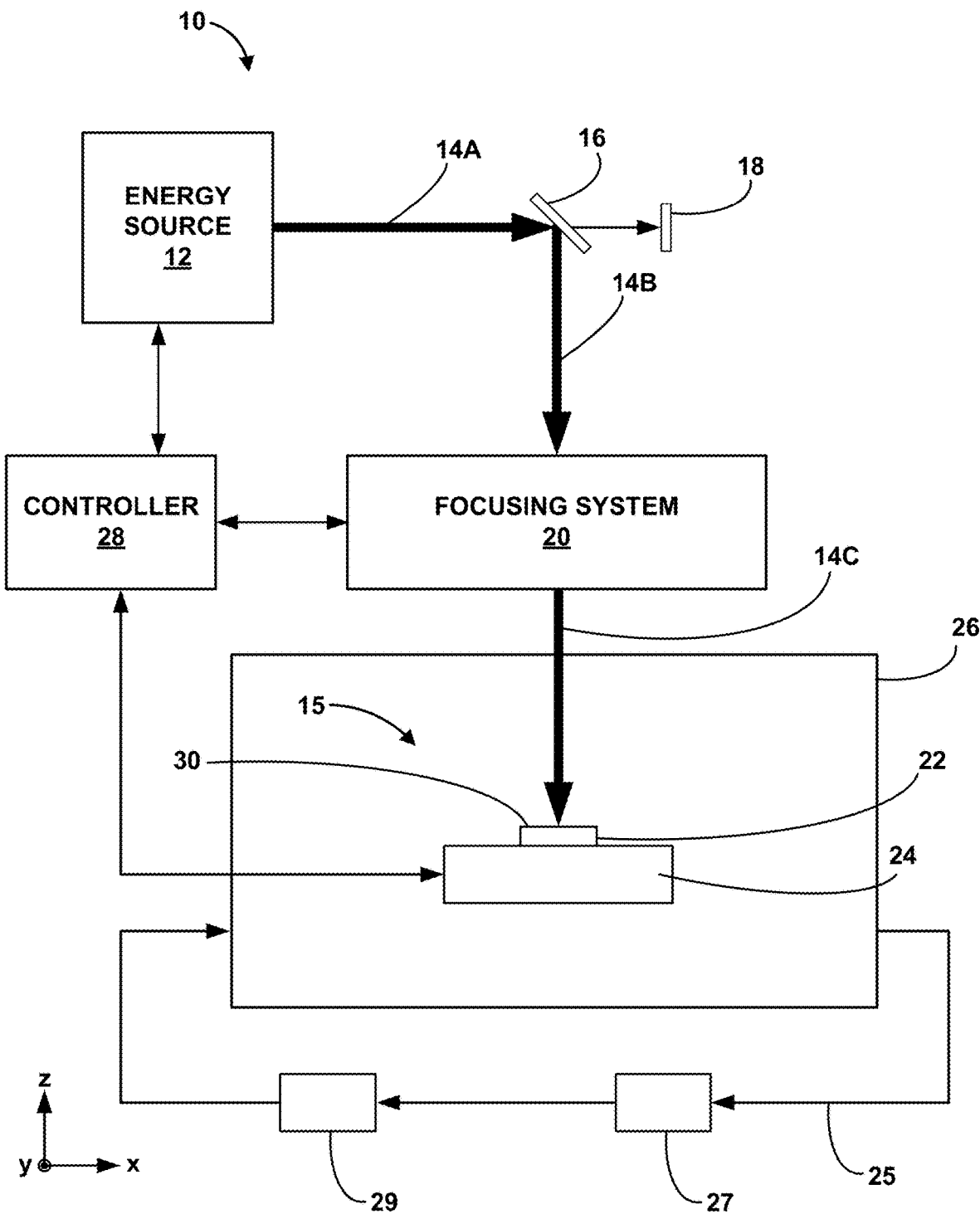
FIG. 1 is a conceptual diagram illustrating an example energy pulse texturing system, in accordance with one or more aspects of this disclosure.

FIG. 1 is a conceptual diagram illustrating an example energy pulse texturing system 10, in accordance with some examples of this disclosure. System 10 includes an energy source 12, a focusing system 20, tubing 25, a chamber 26, a reservoir 27, a controller 28, and a pump 29. Energy source 12 outputs energy pulse 14A to focusing system 20, e.g., via an optional mirror 16. Focusing system 20 focuses a focal volume of a focused energy pulse 14B at or near a surface 30 of a metallic substrate 22 enclosed inside chamber 26. Metallic substrate 22 may be held on a stage 24 and placed in contact with a liquid, e.g., liquid 15, when being exposed to focused energy pulse 14B to create surface texturing. Pump 29 may circulate the liquid from reservoir 27 into and out of chamber 26 via tubing 25.

Energy source 12 may include, for example, a laser source. In some examples, energy source 12 may be a regeneratively amplified Ti-sapphire or a fiber laser system.

Energy source 12 may output energy pulses 14A with selected parameters including pulse duration, wavelength, energy, and repetition rate. In some examples, energy source 12 may output energy pulses 14A with a pulse duration in the femtosecond or picosecond range, or shorter. For example, the pulse duration of energy pulses 14A may be between about 5 femtoseconds and about 500 picoseconds. In some examples, energy source 12 may output energy pulses 14A with a pulse duration between about 300 and about 360 femtoseconds. The pulse duration may affect a peak power delivered by energy pulses 14A. In some examples, energy pulses 14A having a pulse length of nanoseconds or longer may result in a different surface texture than energy pulses 14A having a pulse duration in the femtosecond or picosecond range.

Energy source 12 may output energy pulses 14A with a selected wavelength or range of wavelengths. For example, energy source 12 may output energy pulses 14A with a wavelength between about 200 nanometers (nm) and about 2000 nm. For example, a wavelength of energy pulses 14A may be about 343 nm, about 515 nm, or about 1030 nm.

Energy source 12 may output energy pulses 14A with a selected energy per pulse. For example, the energy per pulse of energy pulses 14A may be between about 1 microjoule (µJ) and about 200 µJ. For example, the amount of energy in energy pulses 14A may be between about 5.0 µJ and about 50.0 µJ.

Energy source 12 also may output energy pulses 14A at a selected repetition rate. The repetition rate refers to the number of pulses per second, and also may be referred to as the pulse frequency. In some examples, energy source 12 may output energy pulses 14A at repetition rate between about 1 hertz (Hz) and about 2 megahertz (MHz), such as about 100 kilohertz (kHz).

Energy source 12 may output energy pulses 14A with the selected parameters to focusing system 20. In some examples, prior to reaching focusing system 20, energy pulses 14A may encounter a mirror 16. In some examples, mirror 16 may be a beam splitter and/or a waveplate, which may reflect a portion of energy pulses 14A to form reflected energy pulses 14B, which are directed to focusing system 20. A second portion of energy pulses 14A may transmit through the beam splitter, e.g., to a beam stop 18 or an absorber. In this way, the beam splitter may be used to select a certain wavelength or, in the case of a polarizing beam splitter, a certain polarization of energy to be reflected to focusing system 20. The beam splitter in combination with the waveplate may control the amount of energy of energy pulses 14A. This may be used to affect an amount of energy passed to focusing system 20 and, ultimately, surface 30.

Reflected energy pulses 14B (or energy pulses 14A in the absence of mirror 16) are then incident on focusing system 20, which may include one or more lenses, mirrors, polarizers, waveplates, diffractive elements, or the like, to shape and focus reflected energy pulses 14B. Focusing system 20 may output focused energy pulses 14C, which may be focused at a surface 30 of metallic substrate 22 or near surface 30 (e.g., in front of or behind surface 30). In this way, focusing system 20 may control whether focused energy pulses 14C are focused at surface 30 or defocused at surface 30, which may affect texturing of surface 30.

Focusing system 20 may focus focused energy pulses 14C to a selected volume, which may be defined by an average energy. In some examples, focused energy pulses 14C exhibits a three-dimensional Gaussian spatial profile of energy with a peak at the center of the focal volume. The focal volume may be positioned at a first position at surface 30 of metallic substrate 22, at a second position in front of surface 30 (nearer to focusing system 20 than surface 30 is), or at a third position behind surface 30 (further from focusing system 20 than surface 30 is), where the second and third positions generate defocus at the metallic surface. In some examples, the focal volume of focused energy pulses 14C may have a diameter between about 5 micrometers (µm) and about 200 µm. In some examples, the focal volume of focused energy pulses 14C may be about 20 µm.

Instead of focal volume, focused energy pulses 14C may be characterized by a selected intensity. The intensity refers to the energy per area. In some examples, energy source 12 may output energy pulses at an intensity between about 0.01 joules per square centimeter ($J/cm^2$) and 50 $J/cm^2$.

In some examples, focusing system 20 may direct focused energy pulses 14C to surface 30 in a direction substantially normal to surface 30. In other examples, focusing system 20 may direct focused energy pulses 14C to surface 30 in a non-normal direction.

System 10 also includes chamber 26 and stage 24. Chamber 26 is configured to contain a liquid, such as water, hydrogen peroxide, ammonium hydroxide, an amine, an alcohol, silicone oil, acetic acid, a carboxylic acid, a mineral acid, a ketone, an ester, an organic fluid, or the like, and any combination thereof. In some examples, as shown in FIG. 1, chamber 26 also encloses stage 24 and metallic substrate 22. In other examples, chamber 26 may enclose metallic substrate and may contact a surface of stage 24 without fully enclosing stage 24. In still other examples, chamber 26 may contact surface 30 and contain liquid in contact with a portion of surface 30.

Chamber 26 may include one or more ports through which liquid may be added, removed, or both. In some examples, chamber 26 may be open to atmosphere, such that the liquid is open to the atmosphere and focused energy pulse 14C enter the liquid through the atmosphere. In other examples, chamber 26 may be substantially fully enclosed, and may include a cover that is substantially transparent to the wavelength of focused energy pulses 14C, through which focused energy pulses 14C may enter the interior of chamber 26. In some examples, the liquid contained in chamber 26 may be volatile, cause safety concerns, or damage the optics, such as damaging the focusing lens. In which case, chamber 26 may be substantially fully enclosed to ensure the volatile liquid may be contained and reduces concerns.

The liquid contained in chamber 26 may be selected based on the effect of the liquid on the surface texturing technique. For example, water may have a higher heat transfer coefficient than air or nitrogen gas, and thus may cool surface 30 of metallic substrate 22 more quickly after surface 30 is exposed to focused energy pulses 14C. This may result in a different surface texture being imparted to surface 30. As another example, the liquid may absorb a portion of the energy of focused energy pulses, thus lowering the energy to which surface 30 is exposed, again resulting in a different surface texture being imparted to surface 30 for a given set of energy pulse parameters.

In some examples, the liquid also may react with metallic substrate 22 upon exposure to focused energy pulses 14C to chemically modify surface 30. For example, an oxygen-containing liquid like water or hydrogen peroxide may release oxygen, which reacts with metal in metallic substrate 22 to form a metal oxide on surface 30. As another example, a nitrogen-containing liquid like ammonium hydroxide may release nitrogen, which reacts with metal in metallic substrate 22 to form a metal nitride on surface 30. In this way, the techniques described herein may in some example accomplish surface texturing and chemical modification in a single operation.

Metallic substrate 22 may be at least partially enclosed by chamber 26, such that surface 30 of metallic substrate 22 is in contact with the liquid in chamber 26. Metallic substrate 22 may include any metal or alloy. For example, metallic substrate 22 may include titanium, a titanium alloy, gold, a gold alloy, silver, a silver alloy, platinum, a platinum alloy, stainless steel, a cobalt-chromium alloy, niobium, a niobium alloy, or the like. In some examples, metallic substrate 22 may be used in a medical device. For example, metallic substrate 22 may be an electrode of a medical device, a stent strut, a medical device housing, or the like. In some implementations, metallic substrate 22 may include a titanium foil electrode. In some examples, metallic substrate 22 may be an electrically conducting material, e.g. titanium, niobium, or stainless steel.

Metallic substrate 22 defines surface 30. At least a portion of surface 30 is in contact with the liquid within chamber 26. At least a portion of surface 30 is also textured using focused energy pulses 14C as part of the techniques described herein.

In some examples, metallic substrate 22 is disposed on or coupled to stage 24. Stage 24 supports and optionally restrains metallic substrate 22. For example, stage 24 may include one or more clips or other engagement mechanisms that restrain metallic substrate 22. Additionally, stage 24 may be movable in one or more axes to move metallic substrate 22 relative to focusing system 20 to move focused energy pulses 14C relative to surface 30. For example, stage 24 may be translatable in three orthogonal axes, rotatable around one or more axis, or the like.

Controller 28 is configured and operable to control operation of system 10, including, for example, energy source 12, focusing system 20, and stage 24. Controller 28 may include one or more processors, one or more computing devices, or the like. Processors may include any one or more microprocessors, digital signal processors (DSPs), application specific integrated circuits (ASICs), field-programmable gate arrays (FPGAs), discrete logic circuitry, or any processing circuitry configured to perform the functions attributed to controller 28. The functions attributed to controller 28 or processors described herein, including processing circuitry, may be provided by a hardware device and embodied as software, firmware, hardware, or any combination thereof.

In some examples, controller 28 may include one or more computing devices. A computing device may include, for example, a desktop computer, a laptop computer, a tablet computer, a mobile computing device, a server, a workstation, or the like.

Controller 28 may include or be associated with a memory. Memory may include any volatile or non-volatile media, such as a random-access memory (RAM), read only memory (ROM), non-volatile RAM (NVRAM), electrically erasable programmable ROM (EEPROM), flash memory, and the like. Memory may store computer-readable instructions that, when executed by controller 28, cause processing circuitry to perform various functions described herein. Memory may be considered, in some examples, a non-transitory computer-readable storage medium including instructions that cause one or more processors, such as, e.g., processing circuitry, to implement one or more of the example techniques described in this disclosure. The term "non-transitory" may indicate that the storage medium is not embodied in a carrier wave or a propagated signal. However, the term "non-transitory" should not be interpreted to mean that memory is non-movable. As one example, memory may be removed from one device and moved to another device. In certain examples, a non-transitory storage medium may store data that can, over time, change (e.g., in RAM).

Controller 28 may cause energy source 12 to output energy pulses 14A with selected parameters, including, for example, wavelength, pulse duration, repetition rate, energy (or power), and the like. The wavelength may be selected so that focused energy pulses 14C are at least partially absorbed by metallic substrate 22. The pulse duration, repetition rate, and energy or power may be selected to result in delivery of a selected energy per pulse, energy per time, or the like, to metallic substrate 22. In this way, the wavelength, pulse duration, repetition rate, energy (or power), and the like may depend at least in part on the composition of metallic substrate, the composition of the liquid, and the desired surface texture for surface 30.

Controller 28 also may control focusing system 20 to control a focal volume of focused energy pulses 14C, a location of the focal volume relative to surface 30, or the like. For example, controller 28 may control one or more optical elements within focusing system 20 to control a position of the focal volume along the z-axis shown in FIG. 1 to be in front of (so that the focal volume is nearer to focusing system 20 than surface 30 is to focal system 20; also referred to as above), below (so that the focal volume is further from focusing system 20 than surface 30 is from focal system 20; also referred to as behind), or substantially at surface 30. When the focal volume is above or below surface 30, focused energy pulses 14C are defocused at surface 30. When the focal volume is substantially at surface 30, focused energy pulses 14C are focused at surface 30. Whether focused energy pulses 14C are focused or defocused at surface 30 may affect how metallic substrate 22 absorbs the energy pulses, and, thus, may affect the texture imparted to surface 30.

Controller 28 additionally may control focusing system 20, stage 24, or both, to position the focal volume of focused energy pulses 14C in the plane of surface 30 (e.g., parallel to at least one of the x- and y-axes shown in FIG. 1). For example, controller 28 may control focusing system 20, stage 24, or both to raster the focal volume in a predominantly x-axis direction, a predominantly y-axis direction, or both (e.g., a predominantly x-axis direction followed by a predominantly y-axis direction or vice versa). In other examples, controller 28 may control focusing system 20, stage 24, or both to move the position of the focal volume of focused energy pulses 14C in another pattern. The pattern may depend on the desired texture for surface 30, a shape of metallic substrate 22, any existing geometric features in metallic substrate 22 or surface 30, or the like.

Controller 28 may control focusing system 20, stage 24, or both to control a pitch or spacing between adjacent lines, in examples in which the focal volume of focused energy pulses 14C is moved along or parallel to surface 30 in lines. In some examples, controller 28 may control the line pitch to be between about 1 μm and about 500 μm. Energy pulses 14C may be overlapped or not overlapped in both gas and/or liquid conditions. In some examples, the line pitch may be constant across surface 30. In other examples, the line pitch may vary across surface 30.

Controller 28 may control focusing system 20, stage 24, or both to control a scanning speed of focused energy pulses 14C. In some examples, the scanning speed may be between about 0.1 m/s and about 5 m/s. In some examples, the scanning speed may be constant across surface 30. In some examples, scanning speed may be varied throughout the scan, such as decreasing near changes in direction. By controlling the scanning speed, the depth of the surface morphology of surface 30 may be controlled, as the scanning speed relates to the amount of energy delivered to a volume of material at surface 30. When the scanning speed is decreased, there may be more overlap of focused energy pulses 14C, and more energy delivered to a volume of material at surface 30, which may increase the depth of the surface texture of metallic substrate 22. In contrast if the scanning speed is greater, energy pulses may overlap less, and the depth of the surface texture may be less.

Controller 28 also may control the number of cycles of a scanning pattern that are performed. The number of cycles may be at least one, such as 10, 20, 25, 30, 40, 50, or more. More cycles may result in more significant texturing being produced on surface 30.

Focused energy pulses 14C travel from focusing system 20, into the internal volume of chamber 26, through the liquid contained therein, and are incident on surface 30 of metallic substrate 22. Material at or near surface 30 absorbs at least a portion of focused energy pulses 14C. The energy from focused energy pulses 14C causes material at or near surface 30 to heat and melt or sinter, changing a surface texture of surface 30. The amount of heating may be affected by the amount of energy per pulse, the amount of energy delivered to each volume of material, which depends on both the amount of energy per pulse and the scanning speed, the heat transfer coefficients of metallic substrate 30 and the liquid in chamber 26, and the like. For example, by using liquid in chamber 26 instead of gas, the heat transfer coefficient of the environment next to surface 30 may be greater. This leads to faster heat transfer from material next to surface 30 and faster cooling of the material next to surface 30. Faster cooling may lead to less pronounced surface texturing. For example, when using surface texturing parameters that would result in channels being formed in surface 30 when the environment is gaseous, using a liquid environment may result in micro- or nano-scale bubbling of the surface to form a non-uniform roughened texture without defined channels. In this way, using a liquid environment may facilitate texturing surface 30 to form non-uniform texture, increasing the surface area of surface 30. In examples in which metallic substrate 22 is used as an electrode, this may increase capacitance of the electrode and improve performance.

In some examples, in addition to causing surface texturing, focused energy pulses 14C also may cause reactions between one or more elements of metallic substrate 22 and one or more elements of the liquid. For example, in implementations in which the liquid includes water, an alcohol, an acid, an ester, or diluted hydrogen peroxide, focused energy pulses 14C may cause oxidation of one or more elements of metallic substrate 22 by oxygen released from the liquid. As another example, in implementations in which the liquid includes ammonium hydroxide or an amine, focused energy pulses 14C may cause nitridation of one or more elements of metallic substrate 22 by nitrogen released from the ammonium hydroxide. In this way, chemistry of surface 30 may be modified as part of the surface texturing technique.

In some examples, at the same time as or after the surface of metallic substrate 22 is textured, metallic substrate 22 may be nitrided. In some examples, gas nitriding may be completed with a nitrogen rich gas, which may be ammonia. When ammonia comes into contact with a heated element, it disassociates into nitrogen and hydrogen. A nitride layer may be created when the nitrogen diffuses onto the surface of metallic substrate 22 and reacts with the metal or alloy. The controller may select the parameters of system 10, including energy pulse 14A, 14B, and/or 14C, to vary a thickness of the nitride layer. The controller may also control the flow of nitrogen and oxygen into and out of chamber 30 to control the chemical potential of nitrogen in the environment of chamber 30.

In some examples, plasma nitriding may be used to nitride the surface of metallic substrate 22. Electric fields may be used to produce ionized molecules of the gas around the surface of metallic substrate 22. In some examples, the gas may be pure nitrogen. If pure nitrogen is used, spontaneous decomposition may not be required. However, if ammonia is used, spontaneous decomposition may be required. Plasma nitriding may be performed in a temperature range from about 260° C. to more than 600° C.

For example, a reactive gas, such as ammonia or nitrogen plasma, may fill chamber 30 and nitride the surface of metallic substrate 22 while focused energy pulse 14C is texturing the surface of metallic substrate 22. Nitriding the surface of metallic substrate 22 may improve durability and surface chemistry of metallic substrate 22. For example, while texturing with focused energy pulses 14A, the surface chemistry of metallic substrate 22 may be adjusted with titanium nitriding by varying the stoichiometry of the nitrogen.

Figure 2:
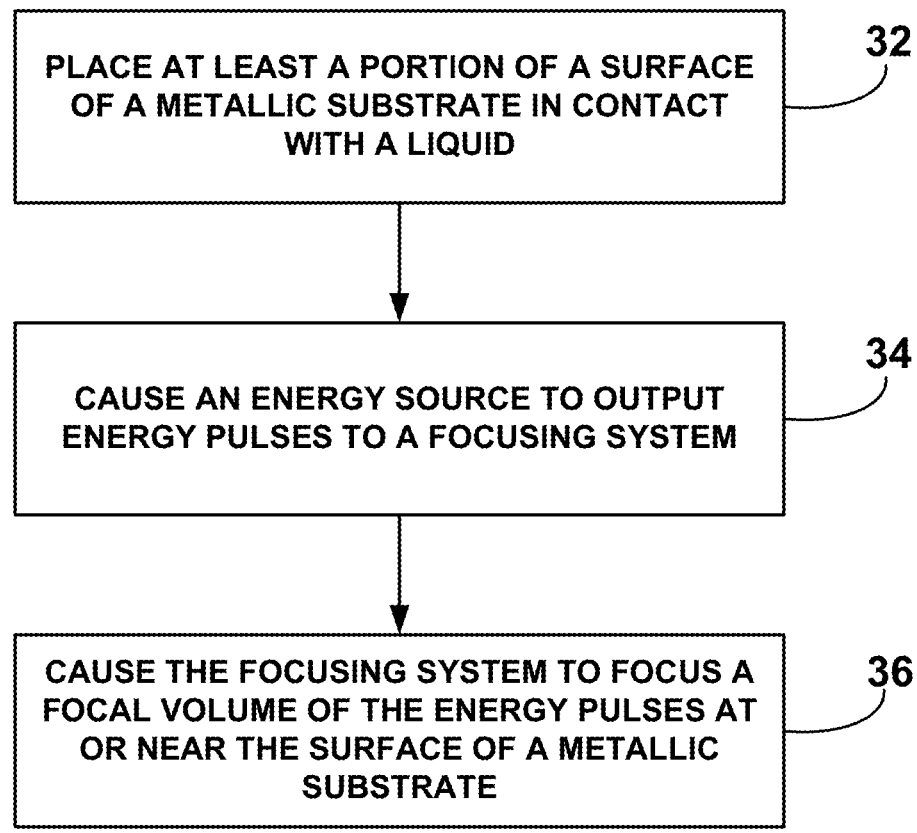
FIG. 2 is a flow diagram illustrating an example process of energy pulse texturing, in accordance with one or more aspects of this disclosure.

FIG. 2 is a flow diagram illustrating an example technique for energy pulse texturing a surface of a metallic substrate, in accordance with one or more aspects of this disclosure. The technique of FIG. 2 will be described with concurrent reference to system 10 of FIG. 1, although a person having ordinary skill in the art will understand that the technique may be performed by another system, and that system 10 may perform other techniques. The technique of FIG. 2 includes placing at least a portion of surface 30 of metallic substrate 22 in contact with a liquid (32). As described above, the liquid may include, for example, water, hydrogen peroxide, ammonium hydroxide, an amine, an alcohol, silicone oil, acetic acid, a carboxylic acid, a mineral acid, a ketone, an ester, an organic fluid, or the like, and any combination thereof. The liquid may be contained in chamber 26. Metallic substrate 22 may be disposed within chamber 26, or chamber may be disposed on surface 30 to maintain contact of the liquid with a portion of surface 30.

The technique of FIG. 2 also includes causing, by controller 28, energy source 12 to output energy pulses 14A to focusing system 20 (34). As described above, controller 28 may cause energy source 12 to output energy pulses 14A with a selected wavelength, pulse duration, pulse energy, repetition rate, and the like.

Controller 28 also causes focusing system 20 to focus a focal volume of focused energy pulses 14C at or near surface 30 of metallic substrate 22 (36). For example, controller 28 may control a position of one or more optical components to control a position of the focal volume in the x-, y-, and/or z-axes shown in FIG. 1. Focused energy pulses 14C may be incident on surface 30 in a focused state or defocused state (e.g., in which the focal volume is in front of or behind surface 30 in the z-axis direction of FIG. 1). Material of metallic substrate 22 at or near surface 30 absorbs at least part of the energy of focused energy pulses 14C, heats, and melts or sinters. The melting or sintering modifies a texture of surface 30 to form micro- or nano-scale surface texturing on surface 30. For example, the micro- or nano-scale surface texturing may include bubble-like surface roughening that increases a surface area of surface 30.

As part of causing focusing system 20 to focus a focal volume of focused energy pulses 14C at or near surface 30 of metallic substrate 22 (36), controller 28 may cause at least one of focusing system 20 and stage 24 to move to scan the focal volume of focused energy pulses 14C in the substantially parallel to surface 30 (e.g., substantially parallel to the x-y plane in FIG. 1). Controller 28 may cause the at least one of focusing system 20 and stage 24 to move in any pattern to scan the focal volume in the pattern. For example, controller 28 may cause focusing system 20 to move to cause the focal volume to scan surface 30 in a raster pattern. The raster pattern may be in predominantly the x-axis direction of FIG. 1 (e.g., the long line path of the raster pattern is substantially parallel to the x-axis), predominantly the y-axis direction of FIG. 1 (e.g., the long line path of the raster pattern is substantially parallel to the x-axis), or at an angle with respect to the x- and y-axes of FIG. 1 (e.g., the long line path of the raster pattern is at an angle to the x- and y-axes). Other patterns are also possible, for example, depending on a geometry of metallic substrate 22 or a shape of a portion of surface 30 that is to be textured. Controller 22 may also control movement of at least one of focusing system 20 and stage 24 to control at least one of a line pitch (e.g., a spacing between adjacent lines traced by the focal volume), a scanning speed of focused energy pulses 14C (e.g., a rate of movement of the focal volume relative to surface 30), or a number of cycles (e.g., a number of times the focal volume traces substantially the same pattern on surface 30). Each of these parameters may affect the texture of surface 30.

In some examples, in addition to causing surface texturing, focused energy pulses 14C also may cause reactions between one or more elements of metallic substrate 22 and one or more elements of the liquid. For example, in implementations in which the liquid includes water, an alcohol, or diluted hydrogen peroxide, focused energy pulses 14C may cause oxidation of one or more elements of metallic substrate 22 by oxygen released from the water, alcohol or diluted hydrogen peroxide. As another example, in implementations in which the liquid includes ammonium hydroxide, focused energy pulses 14C may cause nitridation of one or more elements of metallic substrate 22 by nitrogen released from the ammonium hydroxide. In this way, chemistry of surface 30 may be modified as part of the surface texturing technique.

Figure 3:
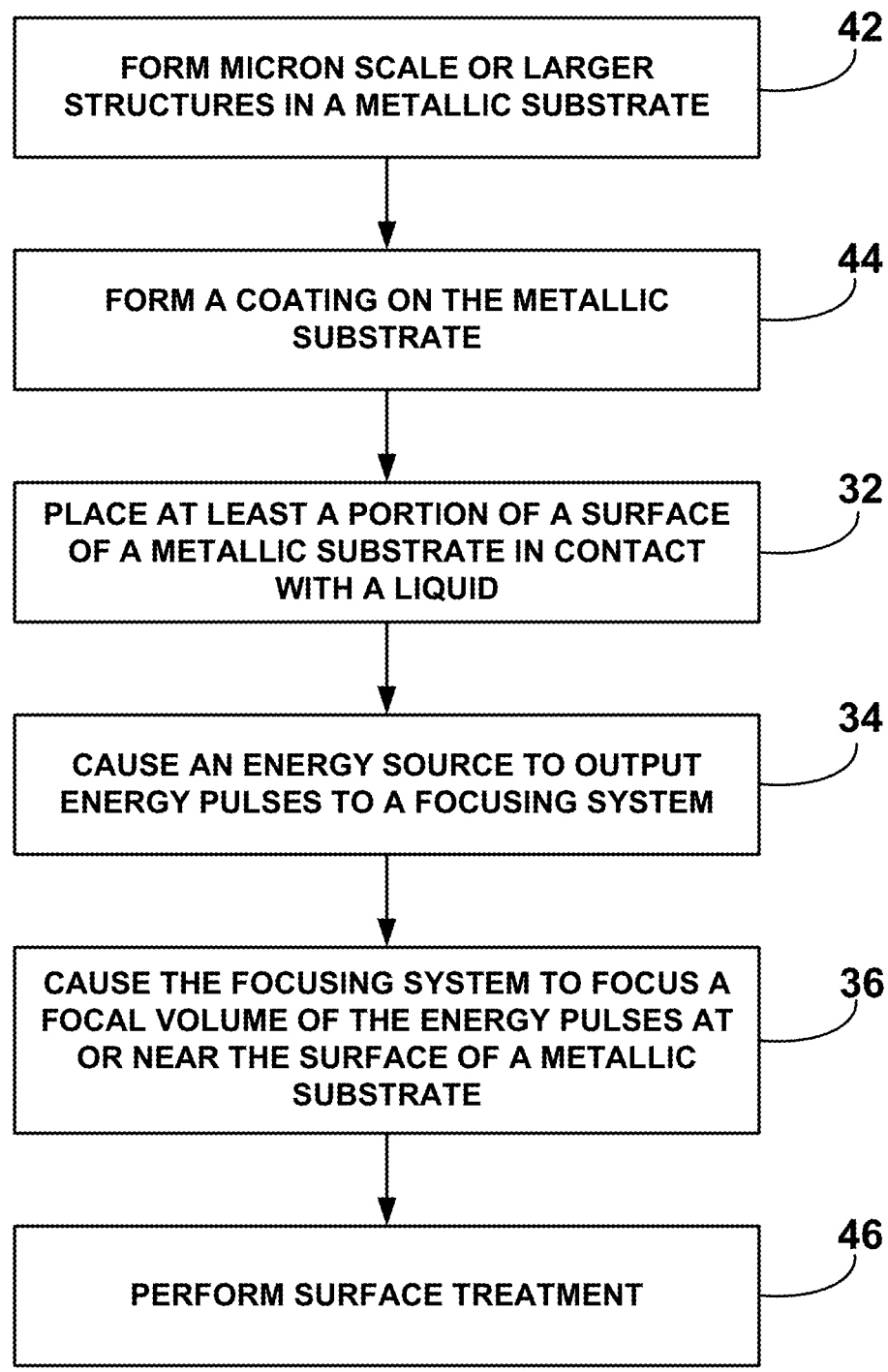
FIG. 3 is a flow diagram illustrating an example process of energy pulse texturing, in accordance with one or more aspects of this disclosure.

In some examples, a surface texturing technique may include other, optional steps in addition to those shown in FIG. 2. For example, FIG. 3 is a flow diagram illustrating an example technique for energy pulse texturing, in accordance with one or more aspects of this disclosure. The technique of FIG. 3 will be described with concurrent reference to system 10 of FIG. 1, although a person having ordinary skill in the art will understand that the technique may be performed by another system, and that system 10 may perform other techniques. The technique of FIG. 3 includes optional steps before and after the energy pulse texturing in a liquid.

For example, the technique of FIG. 3 optionally includes forming micron scale or larger structures or features in metallic substrate 22 (42). For example, micron scale or larger structures or features may be formed in metallic substrate 22 using etching, machining, casting, molding, additive manufacturing, or the like. Forming micron scale or larger structures or features in metallic substrate 22 (42) may include defining the bulk geometry of metallic substrate 22, defining functional features such as channels, through-holes, grids, or the like, in the metallic substrate 22, or the like.

In some examples, forming micron scale or larger structures or features in metallic substrate 22 (42) may include using energy pulse texturing in a gaseous environment to form micro-scale channels in metallic substrate 22. For example, the gaseous environment may include air, nitrogen gas, or the like. The parameters for the energy pulses may be similar to or substantially the same as described above for energy pulse texturing in the liquid environment. However, rather than chamber 26 being filled with a liquid, chamber 26 may be filled with air, nitrogen gas, or another suitable gas. Controller 28 then may control energy source 12, focusing system 20, and stage 24, as described above to cause focused energy pulses 14C to be incident on surface 30 at selected locations to form channels or other features in surface 30. Example channels are shown below in FIGS. 7A-14B. As shown in those FIGS., the depth and spacing of the channels may depend on the parameters used to form the channels, including, for example, energy per pulse, number of cycles, raster pattern, line pitch, and repetition rate.

Figure 4:
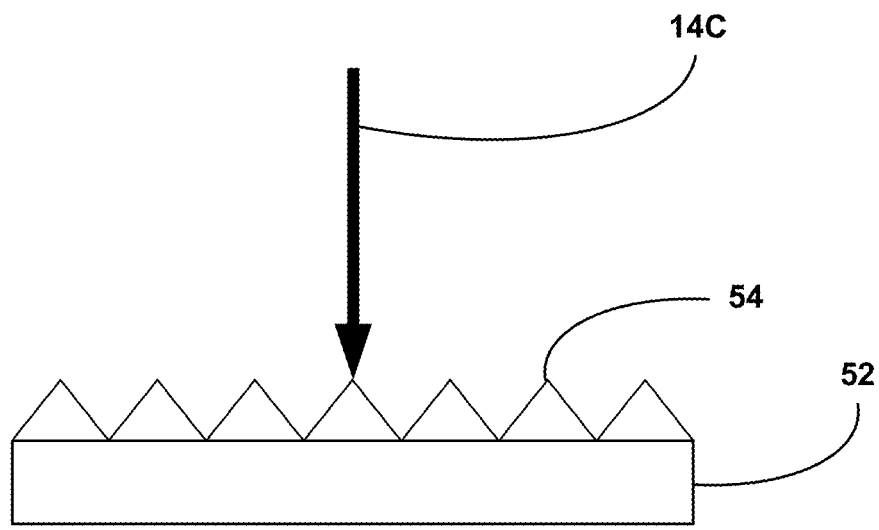
FIG. 4 is a conceptual diagram illustrating an example substrate that includes micro- or macro-scale surface features, in accordance with one or more aspects of this disclosure.

FIG. 4 is a conceptual diagram illustrating, before texturing by focused energy pulses 14C, an example metallic substrate 52 that includes micro- or macro-scale features 54 formed using etching, machining, casting, molding, additive manufacturing, or the like.

The technique of FIG. 3 also optionally includes forming a coating on surface 30 of metallic substrate 22 (44). The coating may provide one or more properties to surface 30, including, for example, hardness, moisture resistance, chemical barrier, dielectric properties, lubricity, or the like. For example, surface 30 may include a parylene coating. In some examples, the coating may be formed on surface 30 prior to forming micron scale or larger structures or features in metallic substrate 22 (42), e.g., when energy pulse texturing in a gaseous environment to form micro-scale channels, as the coating may be substantially transparent to the wavelength of energy used in the energy pulses. The coating may be applied to selected portions of surface 30 and, in some examples, may be omitted from some portions of surface 30. The coating may be applied using any known coating technique, including, for example, gas phase coating techniques (e.g., chemical vapor deposition, physical vapor deposition, sputtering, or the like), spray techniques (e.g., thermal spraying, cold spraying, or the like), spin coating, painting, dip coating, or the like.

The technique of FIG. 3 then includes placing at least a portion of surface 30 of metallic substrate 22 in contact with a liquid (32), causing, by controller 28, energy source 12 to output energy pulses 14A to focusing system 20 (34), and causing, by controller 28, focusing system 20 to focus a focal volume of focused energy pulses 14C at or near surface 30 of metallic substrate 22 (36). Each of these steps may be similar to or substantially the same as the corresponding step from FIG. 2. In some examples in which a metallic substrate includes pre-formed micro- or macro-scale features, like metallic substrate 52 of FIG. 4, controller 28 may cause focusing system 20 to a focal volume of focused energy pulses 14C at or near surface 30 of micro- or macro-scale features 54, as shown in FIG. 4.

The technique of FIG. 3 also may optionally include performing a surface treatment (46). In some examples, the surface treatment may include anodizing. In some examples, metallic substrate 22 may be anodized by immersing metallic substrate 22 in an electrolytic solution. A direct current may be passed through the solution between metallic substrate 22 serving as the anode and a cathode immersed in the solution. The direct current releases oxygen at the surface of metallic substrate 22, building up an oxide layer on the surface of metallic substrate 22.

In some examples, the surface treatment may include plasma nitriding. Electric fields may be used to produce ionized nitrogen molecules from a nitrogen-rich gas, such as nitrogen or ammonia, near surface 30. Plasma nitriding may be performed at a temperature range from about 260° C. to more than 600° C.

In this way, energy pulse texturing of surface 30 in contact with a liquid may be used alone or in combination with one or more additional processing techniques to create desired texturing on surface 30. Energy pulse texturing of surface 30 in contact with a liquid may be used to reduce a number of processing steps for preparing metallic substrate 22 (e.g., by combining texturing and surface chemistry modification), make surface 30 more resistant to scratches (e.g., by forming a well-adhered coating by combining texturing and surface chemistry modification), allow selective surface texturing without a prior masking step, allow surface texturing after application of other coatings (e.g., parylene), or the like.

Figure 5:
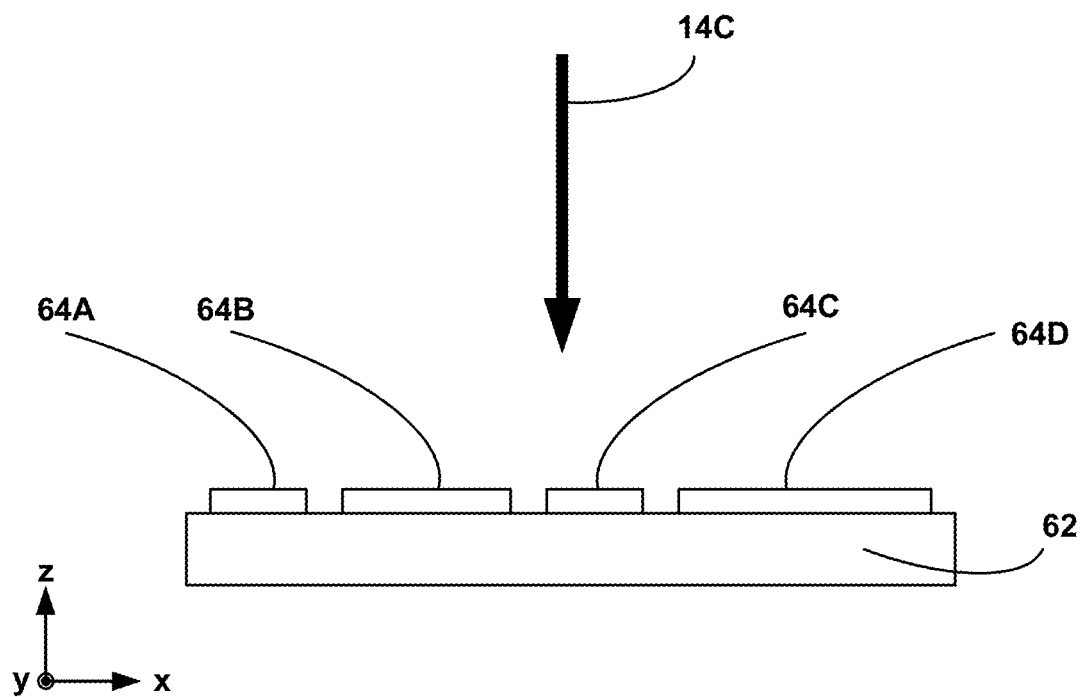
FIG. 5 is a conceptual diagram illustrating an example substrate that includes multiple electrodes, in accordance with one or more aspects of this disclosure.

FIG. 5 is a conceptual diagram illustrating an example metallic substrate 62 that includes multiple electrodes 64A, 64B, 64C, and 64D (collectively known as electrodes 64). Each electrode 64 may be textured by focused energy pulses 14C with a different process by varying the process environment, including the liquid, such as water, hydrogen peroxide, ammonium hydroxide, an amine, an alcohol, silicone oil, acetic acid, a carboxylic acid, a mineral acid, a ketone, an ester, an organic fluid, or the like, and any combination thereof, and/or the energy pulse parameters, such as pulse duration, wavelength, focal volume, scan speed, number of cycles, line pitch, or the like, and any combination thereof, to generate different three-dimensional surface texture features. In some examples, each electrode 64 may be treated differently at locations along the surface of electrode 64. For example, each electrode 64 may be treated to three different process environment and energy source parameters along a predominantly y-axis direction. Electrodes 64 may be separated by a dielectric material (e.g., an electrically insulating polymer, oxide, or the like).

Figure 6:
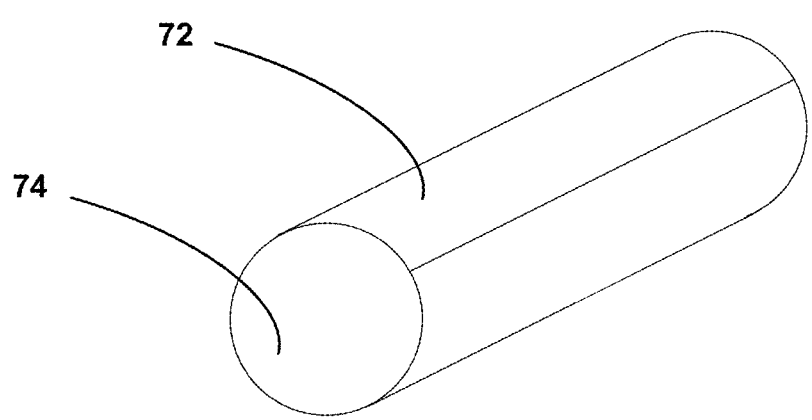
FIG. 6 is a conceptual diagram illustrating an example three-dimensional electrode surface, in accordance with one or more aspects of this disclosure.

FIG. 6 is a conceptual diagram illustrating an example three-dimensional electrode surface. In some examples, as shown in FIG. 6, a metallic substrate 72 may have a substantially cylindrical shape and be positioned around or surrounding a lead body 74. While a cylinder is shown with a circular cross section, the cross section may be elliptical or otherwise deviate from a circular shape. In some examples, rather than fully surrounding lead body 74, an electrode may partially surround a perimeter of lead body 74 and may define an arc-shaped or parabolic cross-section.

EXAMPLES

Comparative Examples 1-5

FIGS. 7A-7E are images illustrating samples of Grade 1 Ti foils energy textured in air. FIGS. 7A-7E reveal how changing the number of cycles (number of scans over the same location) may affect the depth of the texturing, while keeping other variables constant. The energy texturing was performed using a Satsuma HP3 fiber laser (available from Amplitude Systemes, Pessac, France). The Satsuma laser was operated with a pulse duration of about 360 femtoseconds, a wavelength of about 1030 nanometers, a focal volume of about 20 micrometers, a focal length of the f-theta lens of about 100 millimeters, and a scan speed of about 100 millimeters per second. Optical images of the textured substrates were collected using an Olympus LEXT laser confocal microscope (available from Olympus Corporation, Tokyo, Japan), and scanning electron microcopy images were collected using a Hitachi SU5000 Schottky Field Emission Scanning Electron Microscope (available from Hitachi High Technologies America, Inc., Chatsworth, California)

Figure 7E:
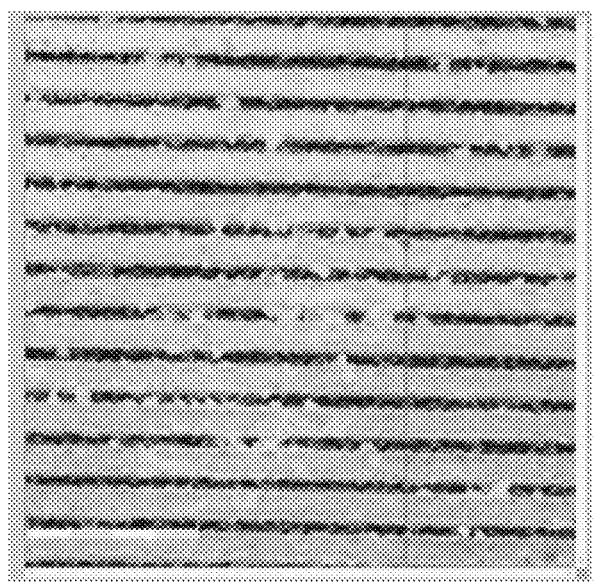

During the surface texturing of the samples illustrated in FIGS. 7A-7E, 8A, and 8B, line pitch was kept constant at about 50 µm, the repetition rate of the energy pulses was kept constant at about 100 kHz, and the energy of the energy pulses was kept constant at about 17.6 µJ. As the number of cycles increased from 1 cycle to about 30 cycles, the depth of the texturing of the Ti foil increased as well, from about 2.7 micrometers (1 cycle; FIG. 7A), to about 20 micrometers (10 cycles; FIG. 7B) to between about 20 and about 40 micrometers (20 cycles; FIG. 7C) to about 40 micrometers (30 cycles; FIG. 7D). But from about 30 cycles (FIG. 7C) to about 40 cycles (FIG. 7E), the depth of the texturing of the Ti foil remained constant at about 40 µm.

FIGS. 8A and 8B are images illustrating Ti foil samples energy textured in air. In particular, FIGS. 8A and 8B are images of the sample shown in FIG. 7B at different levels of magnification. FIG. 8A shows a scale bar of 50.0 μm and FIG. 8B shows a scale bar of 100 μm. As shown in FIGS. 8A and 8B, these processing parameters resulted in well-defined, parallel channels being formed in the Ti foil.

Comparative Examples 6-9

Figure 9A:
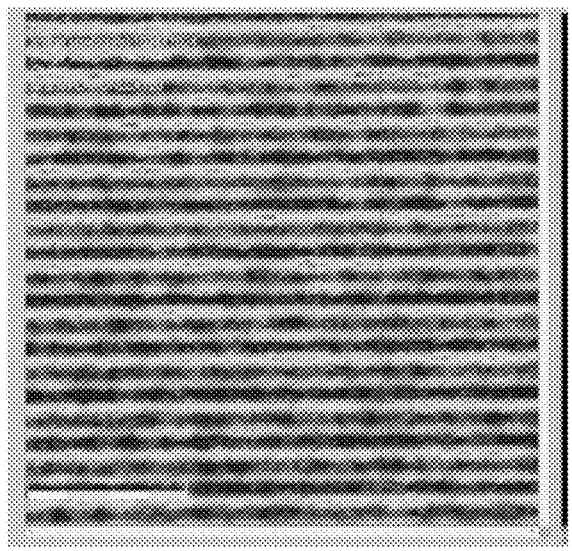
FIGS. 9A-9E are images illustrating samples that have been textured with energy pulses in an air environment.
Figure 9B:
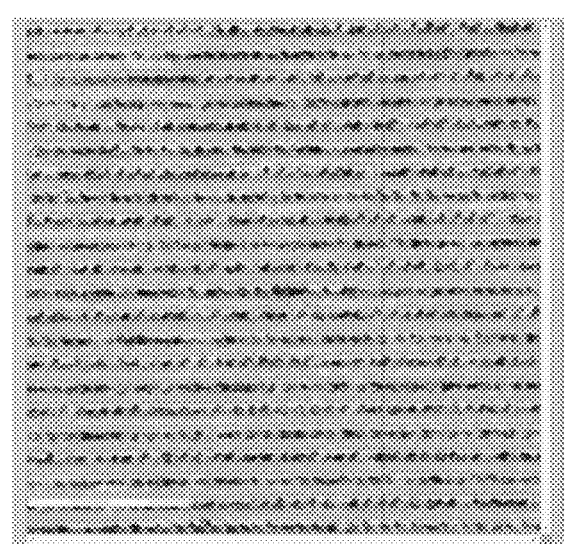
Figure 9C:
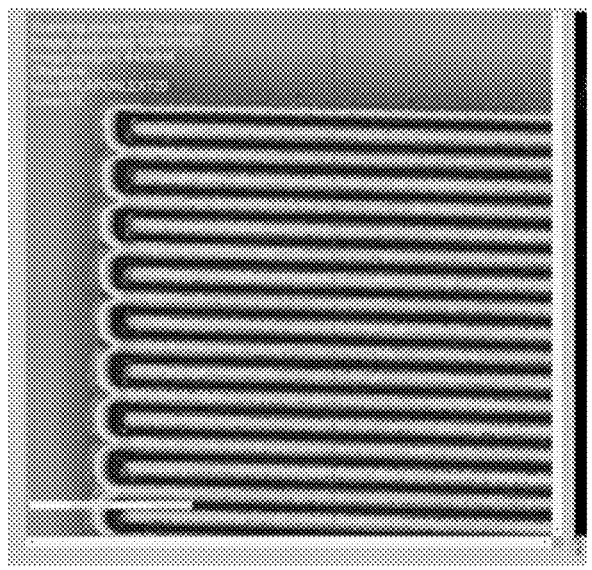
Figure 9D:
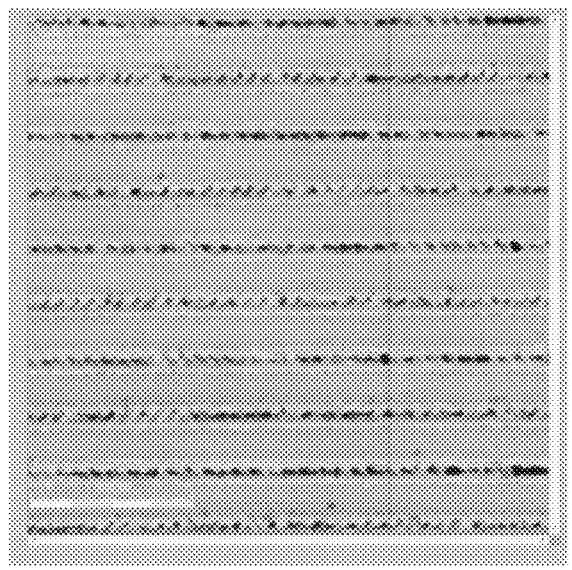
Figure 9E:
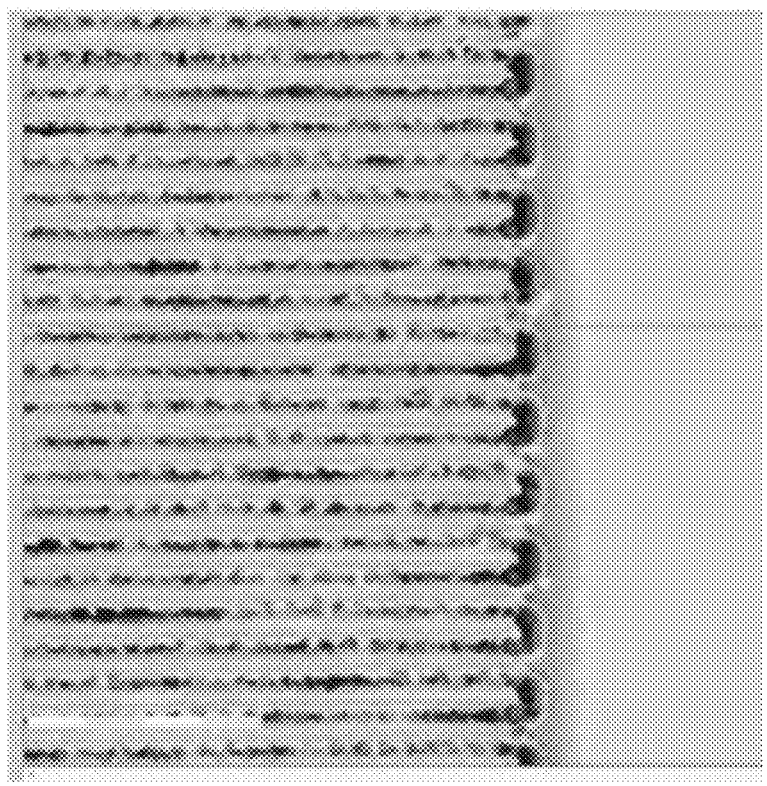

FIGS. 9A-9E are images illustrating samples that have been textured with energy pulses in an air environment. The processing parameters for the sample shown in FIGS. 9A-9E were the same as those described in Comparative Examples 1-5, aside from the differences described herein. FIGS. 9A, 9B, and 9E are carried out with energy pulse parameters including a line pitch of about 30 μm and about 20 cycles. FIG. 9A was prepared using an energy beam defocused by about 500 μm (the stage was lowered by about 500 μm relative to the f-theta lens). Like FIGS. 9A and 9B, FIG. 9D was prepared using about 20 cycles. In contrast to FIGS. 9A and 9B, FIG. 9D was prepared with a line pitch of about 70 μm instead of a line pitch of about 30 μm. The spacing between the channels is visibly different from the line pitch of about 30 μm shown in FIGS. 9A and 9B and the line pitch of about 70 μm shown in FIG. 9D. FIG. 9C shows a micrograph of a sample prepared with a defocused energy beam, a line pitch of about 30 μm, and about 50 cycles. Compared to the images shown in FIGS. 9A, 9B, 9D, and 9E, FIG. 9C has a relatively more well-defined channel. FIG. 9E is a magnified image of the end of the line of the scanning pattern of FIG. 9B. FIG. 9E depicts that a channel may have increased channel depth near locations at which the scanning direction of the energy beam changed due to a reduction in the scanning speed. FIGS. 9A-9E show that an increase in the number of cycles may create more well-defined surface morphologies including channels.

Comparative Example 10

Figure 10A:
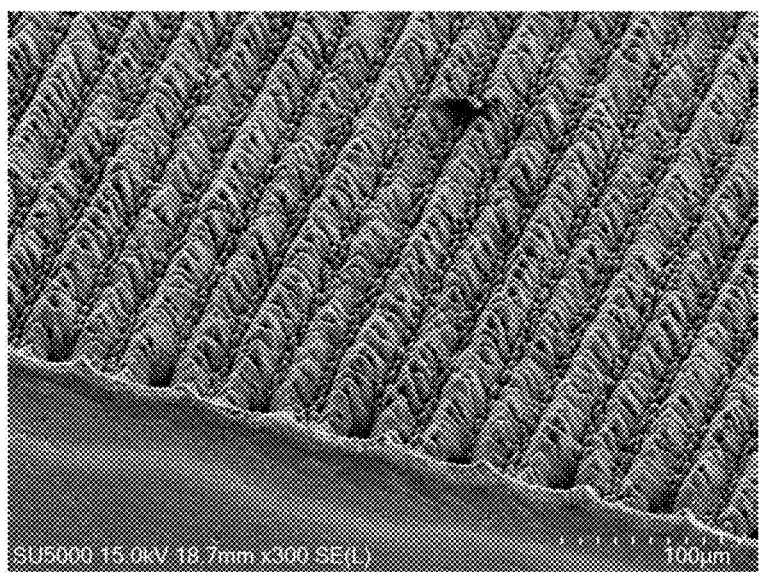
FIGS. 10A-10C are images at different magnification levels of a sample prepared using a defocused energy beam.
Figure 10B:
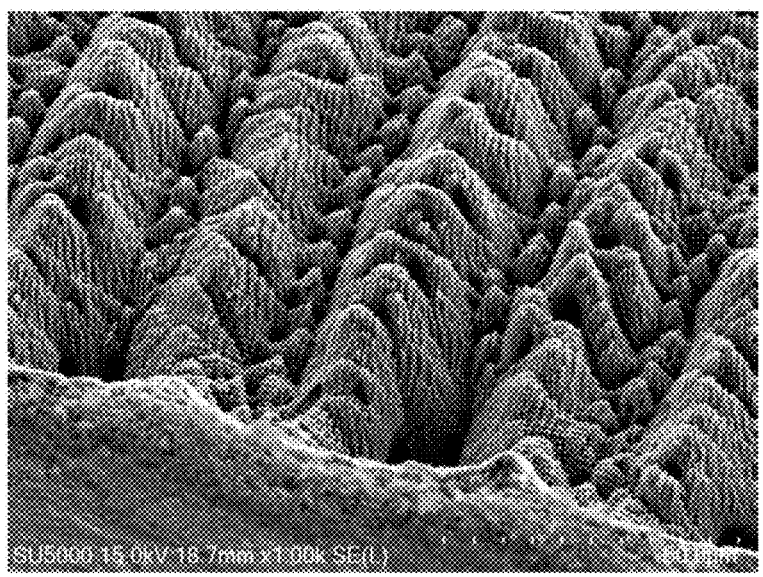
Figure 10C:
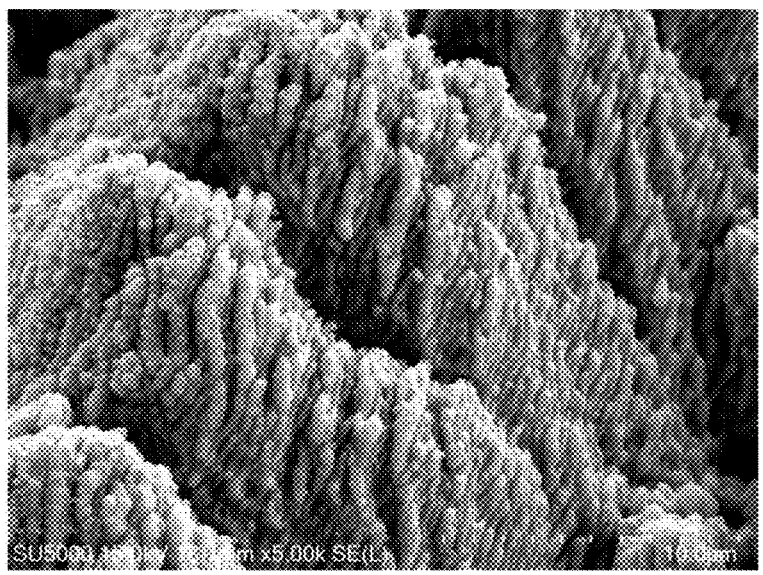

FIGS. 10A-10C are images at different magnification levels of a sample prepared using a defocused energy beam. The processing parameters for the sample shown in FIGS. 10A-10C were the same as those described in Comparative Examples 1-5, aside from the differences described herein. The line pitch was about 30 μm, the number of cycles was about 50, the pulse energy was about 17.6 μJ, and the energy beam was defocused by moving the stage by about 500 μm relative to the focal spot of the f-theta lens. By comparing FIGS. 8A and 8B to FIGS. 10A-10C, the varying surface morphologies that may be created by changing the energy pulse parameters are shown. For example, FIGS. 10A-10C show the surface morphologies as individual peaks or cone-like shapes, and FIGS. 8A and 8B show the surface morphologies that may be described as a trench or channel.

Comparative Example 11

Figure 11A:
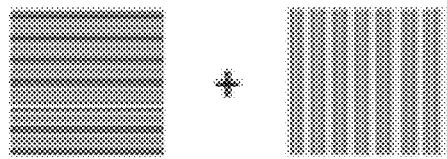
FIG. 11A is a conceptual diagram illustrating a raster pattern that includes both a scan in a predominantly x-axis direction and a scan in a predominantly y-axis direction.
Figure 11B:
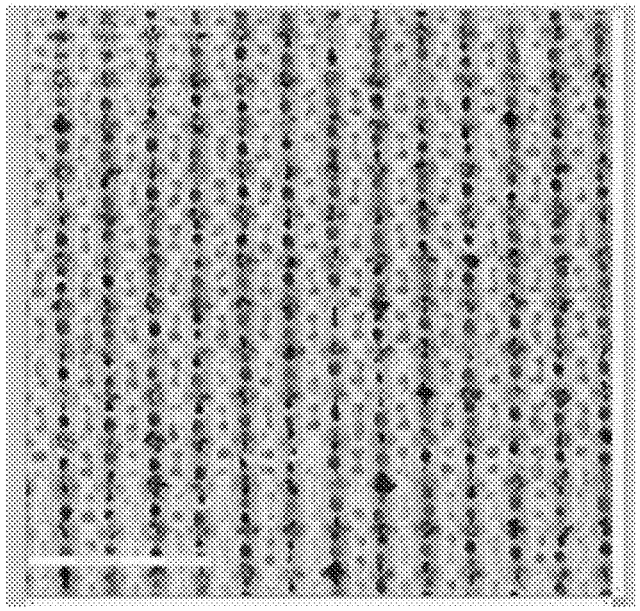
FIGS. 11B-11D are micrographs of surface morphology of substrates textured with energy pulses and the scan pattern shown in FIG. 11A, taken at different magnifications.
Figure 11C:
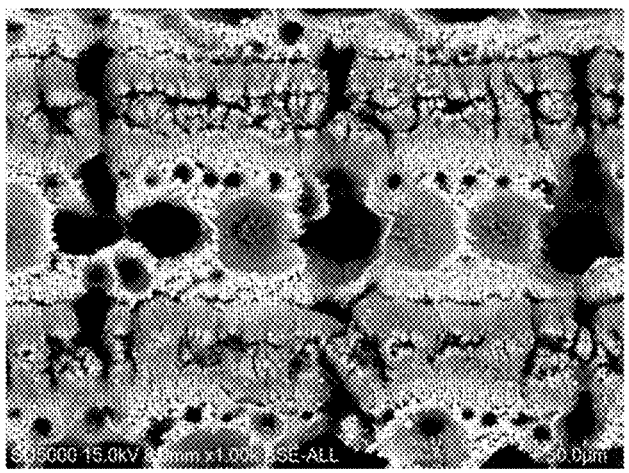
Figure 11D:
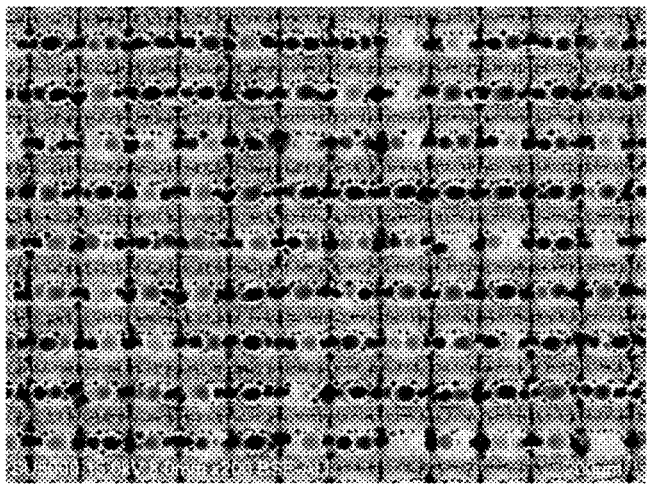

FIG. 11A is a conceptual diagram illustrating a raster pattern that includes both a scan in a predominantly x-axis direction and a scan in a predominantly y-axis direction. The scan pattern shown in FIG. 11A was used to prepare the samples shown in FIGS. 11B-11D. The processing parameters for the sample shown in FIGS. 11B-11D were the same as those described in Comparative Examples 1-5, aside from the differences described herein. FIGS. 11B-11D are micrographs of surface morphology of substrates textured with energy pulses using about 20 cycles and the scan pattern shown in FIG. 11A, taken at different magnifications. After the Ti foil was textured with the x-axis and y-axis scans, the Ti foil includes overlapping trenches in a grid-like pattern.

Comparative Examples 12 and 13

FIGS. 12A and 12B are micrographs of surface morphology on substrates completed with energy pulses in a nitrogen environment and a different number of cycles. The processing parameters for the samples shown in FIGS. 12A-13B were the same as those described in Comparative Examples 1-5, aside from the differences described herein. For the sample shown in FIG. 12A, energy pulse parameters include a line pitch of about 30 μm, about 25 cycles, a pulse energy of about 17.6 μJ, and a defocused beam. For the sample shown in FIG. 12B, energy pulse parameters are the same except for the number of cycles. Instead of about 25 cycles for FIG. 12A, the sample of FIG. 12B was prepared using about 50 cycles. Similar to FIGS. 7A-7E, the samples shown in FIGS. 12A and 12B show the effects of changing the number of cycles while keeping other energy pulse parameters constant. With about twice the number of cycles as the sample shown in FIG. 12A, the sample shown in FIG. 12B shows that an increase in the number of cycles may increase how well-defined the surface morphology of the Ti foil is.

FIGS. 13A and 13B are micrographs at different resolutions illustrating surface morphology on the Ti foil shown in FIG. 12A. FIG. 13A has a resolution scale of 50 μm, and FIG. 13B has a resolution scale of 100 μm. FIGS. 13A and 13B show pyramid-like shapes on the surface of the Ti foil.

Comparative Example 14

FIGS. 14A and 14B are micrographs at different resolutions illustrating surface morphology on a Ti foil completed with energy pulses in a nitrogen environment with a line pitch of about 50 μm, about 25 cycles, and pulse energy of about 17.6 μJ. The other processing parameters for the sample shown in FIGS. 14A and 14B were the same as those described in Comparative Examples 1-5. The image in FIG. 14A is a magnified image of FIG. 14B. FIGS. 14A and 14B illustrate how energy pulse texturing in nitrogen may create well-defined channels tracing a raster pattern of the energy beam.

Example 1

Figure 15:
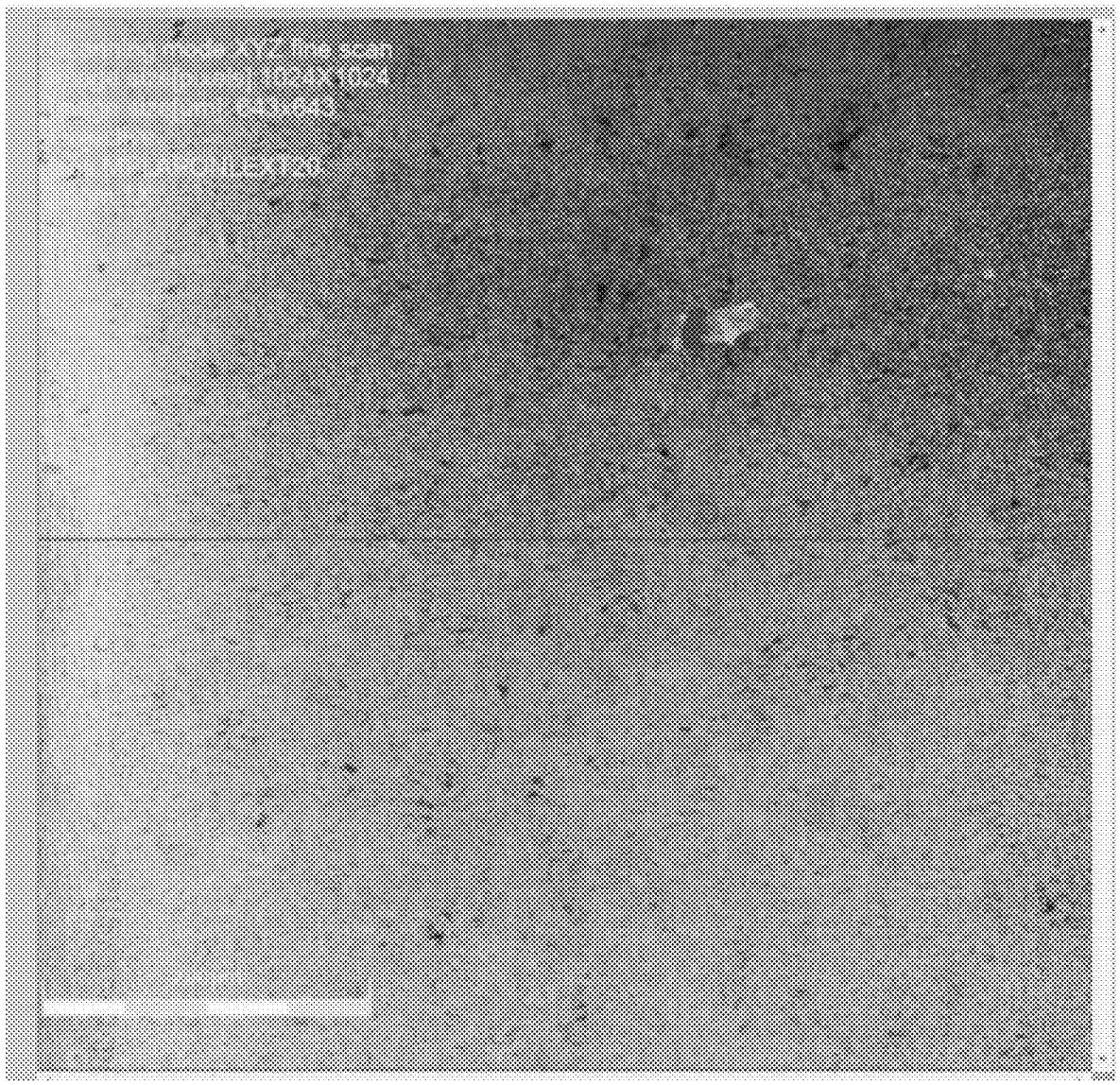
FIG. 15 is a micrograph of surface morphology on a Ti foil energy textured in water.

FIG. 15 is a micrograph of surface morphology on a Ti foil energy textured in water. The processing parameters for the sample shown in FIG. 15 were the same as those described in Comparative Examples 1-5, aside from the differences described herein. The sample was prepared using a line pitch of about 30 μm, an energy pulse repetition rate of about 100 kHz, a pulse energy of about 19.5 μJ, and about 20 cycles. As shown in FIG. 15, energy texturing on the surface of the Ti foil in water does not form trenches as those in air or nitrogen gas. While not wishing to be bound by any theory of operation, this is believed to be due to the absorption of energy pulse by water. Texturing in water primarily creates submicron structures that are a few microns deep on the surface of the Ti foil.

Example 2

FIGS. 16A and 16B are micrographs at different magnifications illustrating surface morphology of a Ti foil energy textured in water. The processing parameters for the sample shown in FIGS. 16A and 16B were the same as those described in Comparative Examples 1-5, aside from the differences described herein. The sample illustrated in FIGS. 16A and 16B was prepared with a line pitch of about 30 μm, about 25 cycles, an energy pulse repetition rate of about 100 kHz, and a pulse energy of about 17.6 μJ. As shown by FIGS. 16A and 16B, the surface morphology of the Ti foil textured in the water environment may include bubble-like structures, rather than the channels produced when surface texturing using similar parameters in an air or gaseous nitrogen environment.

Example 3

FIGS. 17A and 17B are micrographs at different magnifications illustrating surface morphology of a Ti foil energy textured in water. The processing parameters for the sample shown in FIGS. 17A and 17B were the same as those described in Comparative Examples 1-5, aside from the differences described herein. The sample illustrated in FIGS. 17A and 17B was prepared with a line pitch of about 50 μm, about 20 cycles, an energy pulse repetition rate of about 100 kHz, and a pulse energy of about 19.5 μJ. The sample illustrated in FIGS. 17A and 17B was thus prepared with a higher pulse energy, a greater line pitch, and fewer cycles than the sample illustrated in FIGS. 16A and 16B. The feature size of the bubbles of the sample illustrated in FIGS. 17A and 17B is less than the sample illustrated in FIGS. 16A and 16B.

Example 4

FIGS. 18A and 18B are micrographs at different magnifications illustrating surface morphology of a Ti foil energy textured in diluted hydrogen peroxide. The processing parameters for the sample shown in FIGS. 18A and 18B were the same as those described in Comparative Examples 1-5, aside from the differences described herein. The sample illustrated in FIGS. 18A and 18B was prepared with a line pitch of about 50 μm, about 25 cycles, an energy pulse repetition rate of about 100 kHz, and a pulse energy of about 17.6 μJ. Similar to FIGS. 15-17B, the surface morphology of the Ti foil illustrated in FIGS. 18A and 18B can be described as bubble-like.

Example 5

FIGS. 19A and 19B are micrographs at different magnifications illustrating surface morphology of a Ti foil energy textured in diluted hydrogen peroxide. The processing parameters for the sample shown in FIGS. 19A and 19B were the same as those described in Comparative Examples 1-5, aside from the differences described herein. The sample illustrated in FIGS. 19A and 19B was prepared with a line pitch of about 50 μm, about 25 cycles, an energy pulse repetition rate of about 400 kHz, and pulse energy of about 17.6 μJ. Thus, the processing parameters for the Ti foil shown in FIGS. 19A and 19B were substantially similar to those used to prepare the Ti foil shown in FIGS. 18A and 18B, aside from the pulse repetition rate. Similar to the sample in FIGS. 18A and 18B, the surface morphology of the Ti foil in FIGS. 19A and 19B can be described as bubble-like.

Example 6

Figure 20A:
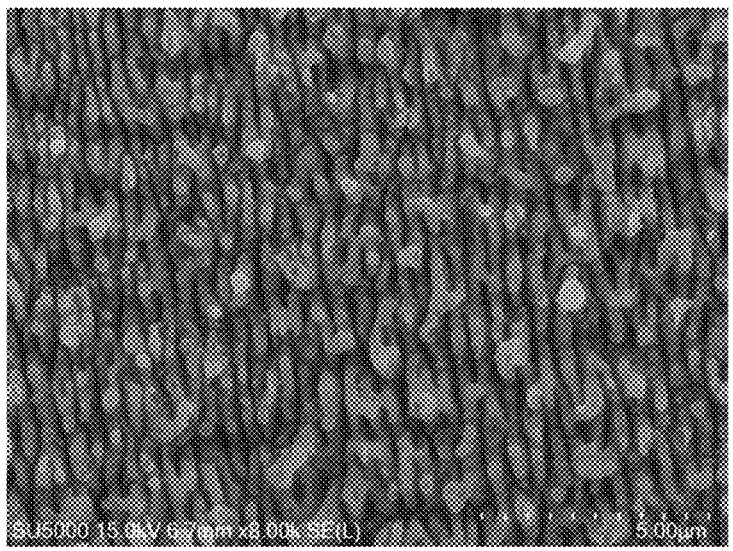
FIGS. 20A-20C are micrographs at different magnifications illustrating surface morphology of a Ti foil energy textured in diluted hydrogen peroxide.
Figure 20B:
Figure 20C:
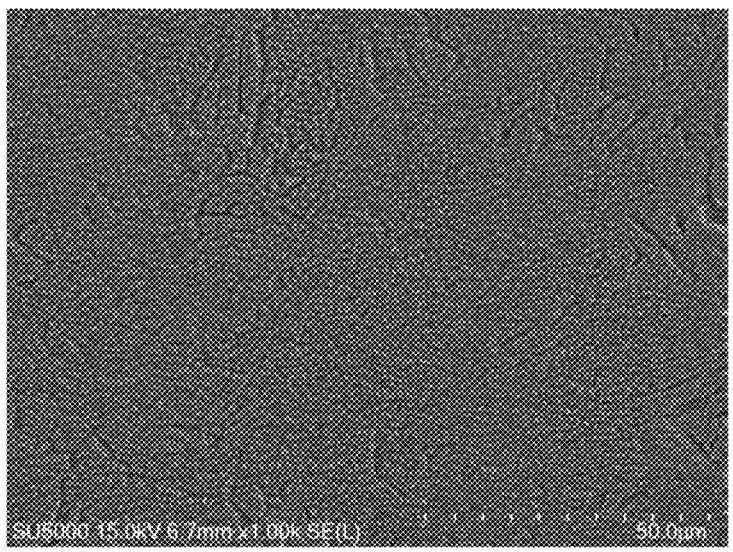

FIGS. 20A-20C are micrographs at different magnifications illustrating surface morphology of a Ti foil energy textured in diluted hydrogen peroxide. The processing parameters for the sample shown in FIGS. 20A-20C were the same as those described in Comparative Examples 1-5, aside from the differences described herein. The sample illustrated in FIGS. 20A-20C was prepared with a line pitch of about 30 μm, about 25 cycles, an energy pulse repetition rate of about 100 kHz, and a pulse energy of about 17.6 μJ. The surface morphology of the Ti foil in FIGS. 20A-20C can be described as bubble-like.

Example 7

Figure 21A:
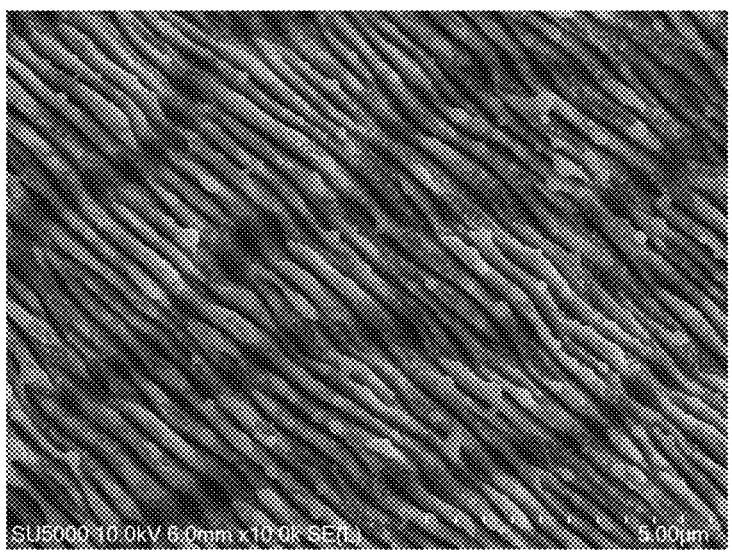
FIGS. 21A-21C are micrographs at different magnifications illustrating surface morphology of a Niobium (Nb) foil energy textured in water.
Figure 21B:
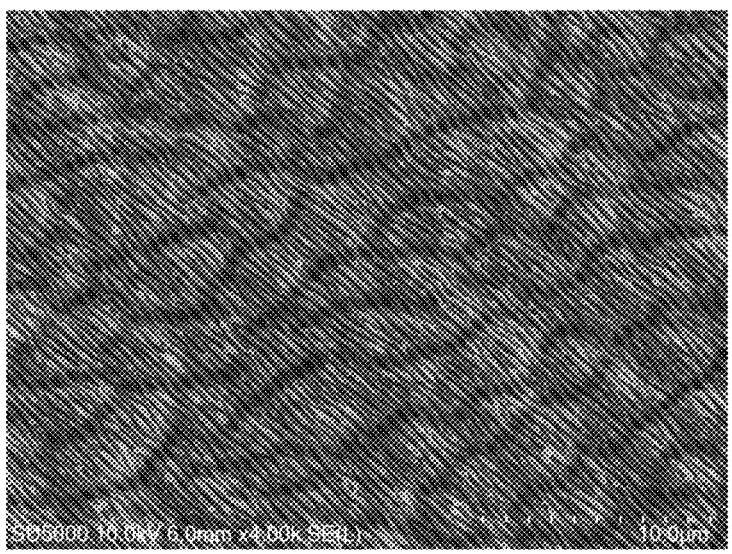
Figure 21C:
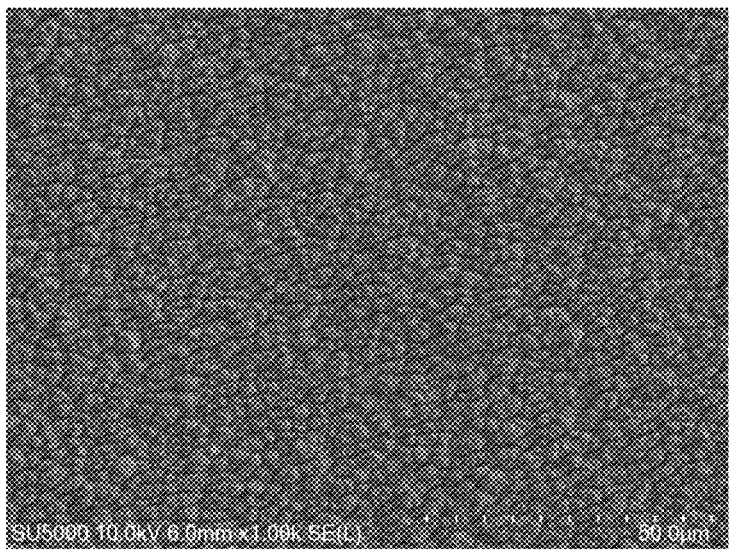

FIGS. 21A-21C are micrographs at different magnifications illustrating surface morphology of a Niobium (Nb) foil energy textured in water. The processing parameters for the samples shown in FIGS. 21A-21C were the same as those described in Comparative Examples 1-5, aside from the differences described herein. The energy texturing was performed using a Tangerine HP fiber laser (available from Amplitude Systemes, Pessac, France). The Tangerine HP laser was operated with a pulse duration of about 300 femtoseconds, a line pitch of about 15 μm, a repetition rate of the energy pulses of about 200 kHz, a pulse energy of about 26 μJ, a scan speed of about 1500 millimeters per second, energy intensity of about 0.2 Joules per square centimeter ($J/cm^2$), and about 300 cycles. The surface morphology of the Nb foil in FIGS. 21A-21C can be described as bubble-like.

Example 8

Figure 22A:
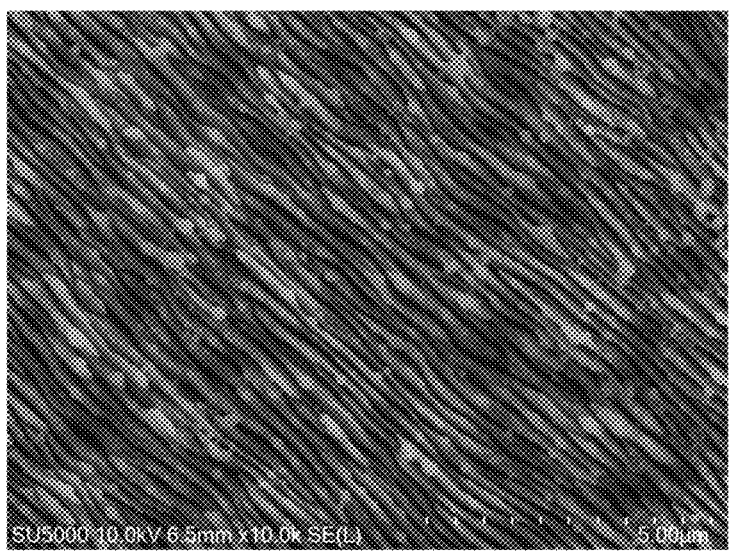
FIGS. 22A-22C are micrographs at different magnifications illustrating surface morphology of a Nb foil energy textured in acetic acid.
Figure 22B:
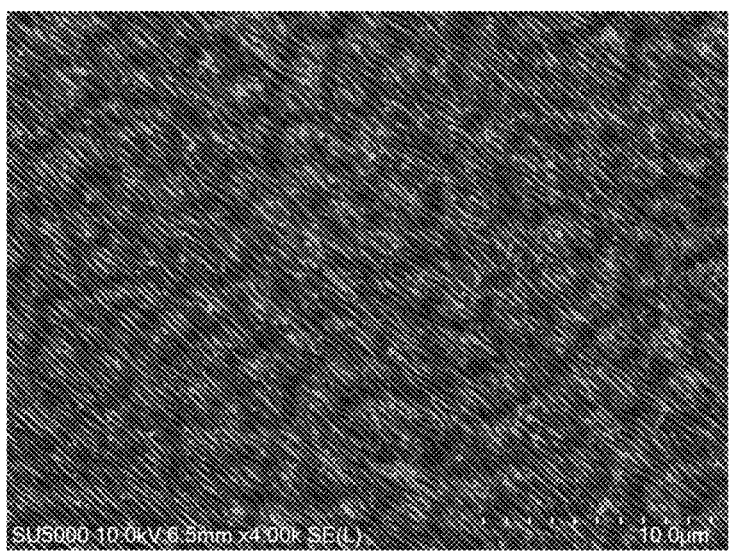
Figure 22C:
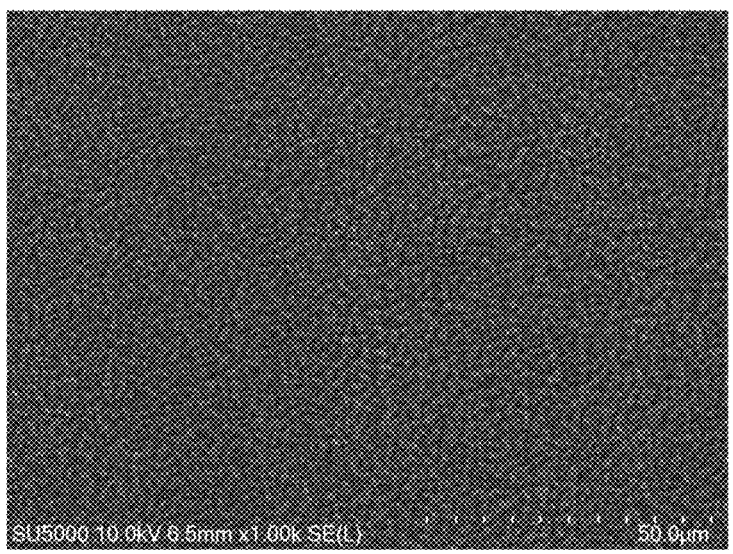

FIGS. 22A-22C are micrographs at different magnifications illustrating surface morphology of a Nb foil energy textured in five percent acetic acid. The processing parameters for the sample shown in FIGS. 22A-22C were substantially the same as those described in Example 7, aside from an energy intensity of about 0.1 $J/cm^2$ and the sample being textured in five percent acetic acid instead of water. The feature size of the bubbles of the sample illustrated in FIGS. 22A-22C is less than the sample illustrated in FIGS. 21A-21C.

Example 9

Figure 23A:
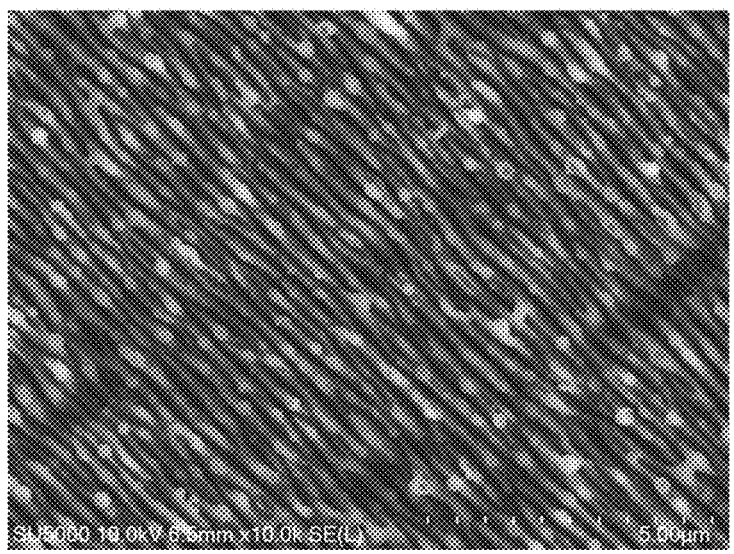
FIGS. 23A-23C are micrographs at different magnifications illustrating surface morphology of a Ti foil energy textured in acetic acid.
Figure 23B:
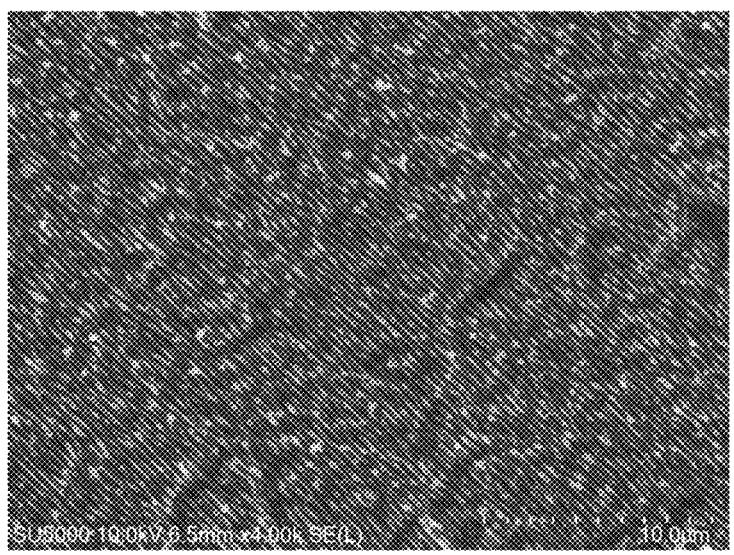
Figure 23C:
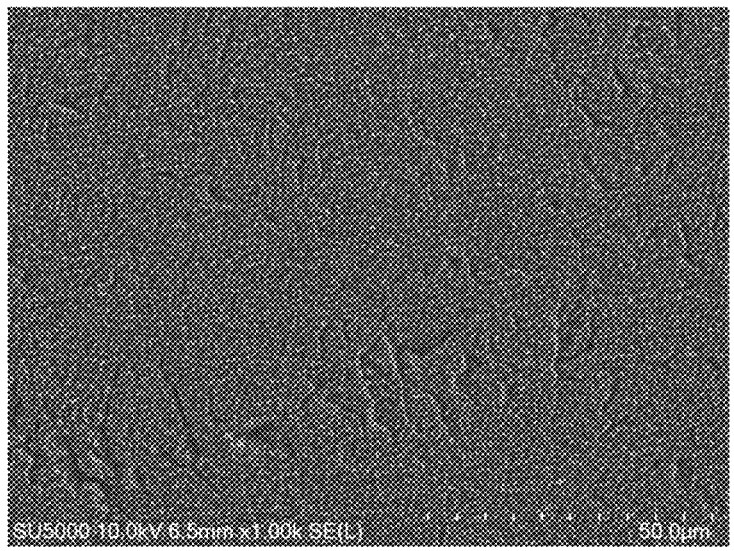

FIGS. 23A-23C are micrographs at different magnifications illustrating surface morphology of a Ti foil energy textured in five percent acetic acid. The processing parameters for the sample shown in FIGS. 23A-23C were substantially the same as those described in Example 7, aside from an energy intensity of about 0.05 $J/cm^2$ and the sample being a Ti foil in five percent acetic acid versus a Nb foil in water.

Various examples have been described. These and other examples are within the scope of the following claims.

What is claimed is:

1. A system comprising:
a focusing system;
an energy source configured to output energy pulses to the focusing system;
a chamber surrounding at least a portion of a metallic substrate and containing a liquid in contact with a surface of the metallic substrate; and
a controller configured to:
cause the energy source to output energy pulses to the focusing system;
cause the focusing system to focus a focal volume of the energy pulses at or near the surface of the metallic substrate that is in contact with the liquid to create micro-scale or smaller surface texturing on the metallic substrate that is less than a thickness of the metallic substrate, cause the focusing system to focus a focal volume of the energy pulses at or near the surface of the metallic substrate that is in contact with the liquid so as to increase a surface area of the surface of the metallic substrate, and cause the focusing system to focus a focal volume of the energy pulses at or near the surface of the metallic substrate that is in contact with the liquid so as to form a surface of the surface texturing having a surface feature size that is based on the liquid being in contact with the surface of the metallic substrate while the focusing system focuses the focal volume at or near the surface of the metallic substrate.

2. The system of claim 1, wherein the energy pulses cause modification of a surface chemistry of the surface of the metallic substrate that is in contact with the liquid.

3. The system of claim 2, wherein the energy pulses cause oxidation of the surface of the metallic substrate that is in contact with the liquid.

4. The system of claim 1, wherein the liquid comprises at least one of water, hydrogen peroxide, ammonium hydroxide, an amine, an alcohol, silicone oil, acetic acid, a carboxylic acid, a mineral acid, a ketone, an ester, and an organic fluid.

5. The system of claim 1, wherein the energy source is configured to output the energy pulses with a femtosecond or picosecond duration.

6. The system of claim 1, further comprising the metallic substrate, wherein the metallic substrate is an electrode of a medical device.

7. The system of claim 6, wherein the controller is configured to cause the energy source to texture more than one electrode located on the metallic substrate to create three-dimensional electrode surfaces by using at least one of different liquids and different energy source parameters.

8. The system of claim 1, wherein prior to the energy pulses creating micro-scale or smaller surface texturing on the metallic substrate, macro-scale and micro-scale structures are formed at or near the surface of the metallic substrate to create a combination of micro-scale and nano-scale features at or near the surface of the metallic substrate.

9. The system of claim 1 wherein the controller is configured to cause the focusing system to change a scanning speed of the focal volume relative to the metallic substrate to change a depth of the surface texturing on the metallic substrate.

10. The system of claim 1, wherein the controller is configured to cause the focal volume and the metallic substrate to move relative to one another in a raster pattern with a line pitch in a range of between about 1 micrometer (μm) and about 500 μm.

11. The system of claim 1, wherein the controller is configured to cause the energy source to control a duration of the energy pulses.

12. The system of claim 1, wherein the controller is configured to cause the energy source to output the energy pulses with an energy intensity range of between about 0.01 Joules per square centimeter ($J/cm^2$) and about 50 $J/cm^2$.

13. The system of claim 1, wherein energy pulses cause the surface of the metallic substrate that is in contact with the liquid to be textured in a substantially non-uniform pattern.

14. The system of claim 2, wherein the liquid comprises at least one of oxygen or nitrogen, and wherein the controller configured to cause the focusing system to focus a focal volume of the energy pulses at or near the surface of the metallic substrate that is in contact with the liquid forming at least one of a metal oxide or a metal nitride on the surface.

* * * * *